(12) United States Patent
Tinnacher et al.

(10) Patent No.: US 8,039,266 B2
(45) Date of Patent: Oct. 18, 2011

(54) METHODS TO RADIOLABEL NATURAL ORGANIC MATTER BY REDUCTION WITH HYDROGEN LABELED REDUCING AGENTS

(75) Inventors: Ruth M. Tinnacher, Lakewood, CO (US); Bruce D. Honeyman, Boulder, CO (US)

(73) Assignee: Colorado School of Mines, Golden, CO (US)

( * ) Notice: Subject to any disclaimer, the term of this patent is extended or adjusted under 35 U.S.C. 154(b) by 897 days.

(21) Appl. No.: 11/856,594

(22) Filed: Sep. 17, 2007

(65) Prior Publication Data

US 2008/0102530 A1    May 1, 2008

Related U.S. Application Data

(60) Provisional application No. 60/845,269, filed on Sep. 15, 2006, provisional application No. 60/845,842, filed on Sep. 18, 2006.

(51) Int. Cl.
  *G01N 33/00* (2006.01)
(52) U.S. Cl. .......................... 436/157; 436/145; 436/146
(58) Field of Classification Search .................... 436/57, 436/145, 146
  See application file for complete search history.

(56) References Cited

U.S. PATENT DOCUMENTS

| | | | |
|---|---|---|---|
| 4,162,142 A | 7/1979 | Ehrenkaufer et al. | |
| 4,649,039 A | 3/1987 | Garlick et al. | |
| 4,795,627 A | 1/1989 | Fisher et al. | |
| 5,073,361 A | 12/1991 | Shroot et al. | |
| 5,186,868 A | 2/1993 | Andres et al. | |
| 5,668,262 A | 9/1997 | Tan et al. | |
| 5,847,104 A | 12/1998 | Tan et al. | |

FOREIGN PATENT DOCUMENTS

| | | | |
|---|---|---|---|
| DE | 3142975 A1 | | 10/1981 |
| DE | 3142975 | * | 5/1983 |

OTHER PUBLICATIONS

Aiken et al., "Isolation of hydrophilic organic acids from water using nonionic macroporous resins," Org. Geochem. vol. 18, No. 4, 1992, pp. 567-573.

Averett et al., "Humic Substances in the Suwannee River, Georgia: Interactions, Properties, and Proposed Structures," USGS Water-Supply Paper 2373, 1994, pp. 217-224.

Banks et al., "A Rapid and Convenient Method for Radiolabeling Detritus with [$^{14}$C]Acetic Anhydride," J. Exp. Mar. Biol. Ecol. vol. 53, 1981, pp. 115-123.

Behrens, H., "Speciation of Radioiodine in Aquatic and Terrestrial Systems under the Influence of Biogeochemical Processes," *Speciation of Fission and Activation Products in the Environment*, Eds. R. A. Bulman and J. R. Cooper, London and New York, Elsevier, 1985, pp. 223-230.

Benner et al., "Preparation, Characterization, and Microbial Degradation of Specifically Radiolabeled [$^{14}$C]Lignocelluloses from Marine and Freshwater Macrophytes," Applied and Environmental Microbiology 47(2), 1984, pp. 381-389.

(Continued)

*Primary Examiner* — Sam P Siefke
(74) *Attorney, Agent, or Firm* — Dorsey & Whitney LLP

(57) ABSTRACT

Methods to radiolabel natural organic matter by reduction with a hydrogen labeled reducing agent, and compositions, are provided.

12 Claims, 9 Drawing Sheets

OTHER PUBLICATIONS

Bubner et al., "Isotopically Labelled Humic Acids for Heavy Metal Complexation," Journal of Labelled Compounds and Radiopharmaceuticals 41, 1998, p. 1057.

Bubner et al., "Synthesis if Isotopically Labeled Synthetic Humic Acids," Annual Report 1998, Institute of Radiochemistry, FZR-247, Eds. H. Nitsche and G. Bernhard, Forschungszentrum Rossendorf, Jan. 1999, p. 25.

Carlsen et al., "Radio-Labelling of Humic and Fulvic Materials for Use in Environmental Studies," Radiochimica Acta 58/59, 1992, pp. 371-376.

Carlsen et al., "Studies on humic acid labelling," Migration of Radionuclide in the Geosphere, 1993, pp. 5-14.

Carrero-Mantilla et al., "Chemical equilibria of multiple-reaction systems from reaction ensemble Monte Carlo simulation and a predictive equation of state: Combined hydrogenation of ethylene and propylene," Fluid Phase Equilibria 242, 2006, pp. 189-203.

Chunxia et al., "The evidence for the incorporation of fulvic acid into the bone and cartilage of rats," The Science of the Total Environment 191, 1996, pp. 197-202.

D'Abramo et al., "Theoretical prediction of thermodynamic equilibrium constants of chemical reactions in water," Journal of Molecular Structure: THEOCHEM 811, 2007, pp. 197-201.

Dierckx, et al., "Stability of $^{125}I$ and $^{14}C$ Labelled Boom Clay Organic Matter," Radiochimica Acta 82, 1998, pp. 379-384.

Esham et al., "Identification and characterization of humic substances-degrading bacterial isolates from an estuarine environment," FEMS Microbiology Ecology 34, 2000, pp. 103-111.

Evans, A. E., "Tritium and its Compounds" Butterworth & Co. Ltd.: Princeton, NJ, Toronto, London, New York, 1966; Chapter 1-3, D. Van Nostrand Company.

Franke et al., "A new technique for radiolabelling of humic substances," Radiochimica Acta 92(4-6), 2004, pp. 359-362.

Gaffney et al., "Humic and Fulvic Acids and Organic Colloidal Materials in the Environment," *Humic and Fulvic Acids: Isolation, Structure, and Environmental Role*, American Chemical Society, D.C., 1996, pp. 2-16.

Gaylord, "Reduction with Complex Metal Hydrides," Interscience Publishers, Inc:, New York, 1956; Chapter 2, 3, 6, 7.

Haider et al., "Phytotron Experiments to Evaluate the Effect of Growing Plants on Denitrification," Soil Science Society of America Journal vol. 49, 1985, pp. 636-641.

Haider et al., "The Effect of Growing Plants on Denitrification at High Soil Nitrate Concentrations," Soil Science Society of America Journal 51(1), 1987, pp. 97-102.

Haider et al., "Mineralization of $^{14}C$-Labelled Humic Acids and of Humic-Acid Bound $^{14}C$-Xenobiotics by *Phanerochaete chryosporium*," Soil Biology and Biochemistry 20(4), 1988, pp. 425-429.

Her et al., "Optimization of Method for Detecting and Characterizing NOM by HPLC—Size Exclusion Chromatography with UV and On-Line DOC Detection," Environmental Science & Technology 2002, 36, pp. 1069-1076.

Higgo et al., "Colloid transport in a glacial sand aquifer. Laboratory and field studies," Colloids and Surfaces A: Physicochemical and Engineering Aspects 73, 1993, pp. 179-200.

Hofrichter, et al., "Mineralization of synthetic humic substances by manganese peroxide from the white-rot fungus *Nematoloma frowardii*," Applied Microbiology and Biotechnology 49, 1998, pp. 584-588.

Ichinose et al., "Preparation of [$4R$-$^3H$]NADH, [$4R$-$^3H$]NADPH and the Corresponding 4S-Isomers All with Substantial Specific Activities," Journal of the Chemical Society, Perkin Transactions 1993, pp. 1213-1216.

Ji et al., "Transformation and mineralization of synthetic $^{14}C$-labeled humic model compounds by soil-feeding termites," Soil Biology & Biochemistry 32, 2000, pp. 1281-1291.

Ji et al., "Digestion of peptidic residues in humic substances by an alkali-stable and humic-acid-tolerant proteolytic activity in the gut of soil-feeding termites," Soil Biology & Biochemistry 37, 2005, pp. 1648-1655.

Kappler et al., "Synthesis and characterization of specifically $^{14}C$-labeled humic model compounds for feeding trials with soil-feeding termites," Soil Biology & Biochemistry 32, 2000, pp. 1271-1280.

Lara et al., "Formation of recalcitrant organic matter: humification dynamics of algal derived dissolved organic carbon and its hydrophobic fractions," Marine Chemistry 51, 1995, pp. 193-1999.

Lassen et al., "Enzymatically mediated incorporation of phenol in humic acids," Finnish Humus News 3, 1991, pp. 221-226.

Lassen, et al., "Radioactive Labelling and Characterization of Humic Materials," Environment International 20(1), 1994, pp. 127-134.

Lassen, et al., "Enzymatically Mediated Incorporation of 2-Chlorophenol and 4-Chlorophenol into Humic Acids," Chemosphere 28(4), 1994, pp. 703-710.

Leenheer et al., "Characterizing Aquatic Dissolved Organic Matter," Environmental Science & Technology 37(1):2003, pp. 18A-26A.

Leenheer, et al., "Presence and potential significance of aromatic-ketone groups in aquatic humic substances," Organic Geochemistry 11(4), 1987, pp. 273-280.

Lenhart, J. J., "The Application of Surface Complexation Modeling to the Adsorption of Uranium(VI) onto Hematite in the Presence of Humic and Fulvic Acids," Ph.D. Dissertation, Colorado School of Mines, Golden, 1997, pp. 118-160.

Lenhart, et al., "Uranium(VI) sorption to hematite in the presence of humic acid," Geochimica et Cosmochimica Acta 63(19/20), 1999, pp. 2891-2901.

Lenz, et al., "Determination of Carbonyl Groups in Oxidatively Modified Proteins by Reduction with Tritiated Sodium Borohydride," Analytical Biochemistry 177, 1989, pp. 419-425.

Li et al., "Selective digestion of the peptide and polysaccharide components of synthetic humic acids by the humivorous larva of *Pachnoda ephippiata* (Coleoptera: Scarabaeidae)," Soil Biology & Biochemistry 37, 2005, pp. 1476-1483.

Lindahl, et al., "Evidence for a 3-$O$-sulfated D-glucosamine residue in the antithrombin-binding sequence of heparin," Proceedings of the National Academy of Sciences, USA 77(11), 1980, pp. 6551-6555.

Ling et al., "Radioassay for RNA $N$-Glycosidase with Tritium-Labeled Sodium Borohydride or Amino Acid," Bioorganic Chemistry 22, 1994, pp. 395-404.

Lippold et al., Investigations on the Influence of Trivalent Electrolytes on Complexation and Adsorption of Heavy Metals with Humic Substances by Means of Radioactive Tracers, Investigations on the complexation behavior of humic acids and their influence on the migration of radioactive and non-radioactive substances under conditions close to nature, Scientific report FZKA 6999, C. M. Marquardt, Forschungszentrum Karlsruhe, 2004, pp. 177-217.

Lippold et al., "Effect of humic acid on the pH-dependent adsorption of terbium (III) onto geological materials," Applied Geochemistry 20, 2005, pp. 1209-1217.

MacCarthy et al., Spectroscopic Methods (other than NMR) for Determining Functionality, *Humic Substances in Soil, Sediment and Water*, New York, John Wiley & Sons: 1985, pp. 527-559.

MacCarthy, The Principles of Humic Substances: An Introduction to the First Principle, *Humic Substances: Structures Models and Functions*, Elham A. Ghabbour, Geoffrey Davies, Eds.; Royal Society of Chemistry, 2001, pp. 19-30.

MacCarthy, "The Principles of Humic Substances" Soil Science 166(11), 2001, pp. 738-751.

Martin et al., "A Comparison of the Use of Phenolase and Peroxidase for the Synthesis of Model Humic Acid-type Polymers," Soil Science Society of America Journal 44(5), 1980, pp. 983-988.

McMurry et al., Fundamentals of Organic and Biological Chemistry, $2^{nd}$ ed., Prentice-Hall, Inc.: Upper Saddle River, NJ, 1999; pp. 141-144.

McMurry, Organic Chemistry, $5^{th}$ ed., Brooks/Cole: Pacific Grove, CA, 2000; pp. 768-769.

Miles, et al., "Stereochemistry of Sodium Borohydride Reduction of Tryptophan Synthase of *Escherichia coli* and Its Amino Acid Schiff's Bases," The Journal of Biological Chemistry 257(23), 1982, pp. 14203-14210.

Murphy, R. J., "Thorium (IV) Binding to Organic and Inorganic Ligands: Marine Colloidal Organic Matter, Marine Polysaccharides and Hematite," Environmental Science and Engineering, Golden, Colorado, Colorado School of Mines: p. 219.

Northcott et al., "Experimental approaches and analytical techniques for determining organic compound bound residues in soil and sediment," Environmental Pollution 108: 2000, pp. 19-43.

Novak et al., "Estimating the Percent Aromatic Carbon in Soil and Aquatic Humic Substances Using Ultraviolet Absorbance Spectrometry," Journal of Environmental Qual. 21: 1992, pp. 144-147.

Periasamy et al., Methods of enhancement of reactivity and selectivity of sodium borohydride for applications in organic synthesis, Journal of Organometallic Chemistry 609, 2000, pp. 137-151.

Pompe et al., "A Comparison of Natural Humic Acids with Synthetic Humic Acid Model Substances: Characterization and Interaction with Uranium(VI)," Radiochimica Acta 74, 1996, pp. 135-140.

Pompe et al., "Determination and Comparison of Uranyl Complexation Constants with Natural and Model Humic Acids," Radiochimica Acta 82, 1998, pp. 89-95.

Pompe et al., "Investigation of humic acid complexation behavior with uranyl ions using modified synthetic and natural humic acids," Radiochimica Acta 88, 2000, pp. 553-558.

Pos et al., "Carbonyl sulfide (OCS) and carbon monoxide (CO) in natural waters: evidence of a coupled production pathway," Marine Chemistry 62, 1998, pp. 89-101.

Quigley et al., "Importance of acid polysaccharides for $^{234}$Th complexation to marine organic matter," Limnol. Oceanogr. 47(2), 2002 pp. 367-377.

The Radiochemical Centre, A., The Radiochemical Manual. $2^{nd}$ ed.; Amersham (Bucks.): Radiochemical Centre: 1966; pp. 42-46.

Ratasuk, Redox functional groups of humic substance. Ph.D. Dissertation, School of Civil Engineering and Environmental Science, University of Oklahoma, 2004.

Rößler et al., "Synthesis and chromatographic characterization of [Tc-99m] technetium-humic acid species," Radiochimica Acta 88, 2000, pp. 95-100.

Rohm et al., The Sodium Borohydride Digest, 2003, 212 pages http://www.hydridesolutions.com/technical.html#.

Sachs et al., "Carbon-13 NMR spectroscopic studies on chemically modified and unmodified synthetic and natural humic acids," Talanta 57, 2002, pp. 999-1009.

Sarkar et al., "Enzymatic Coupling of 2,4-Dichlorophenol to Stream Fulvic Acid in the Presence of Oxidoreductases," Soil Sci. Soc. Am. J. 52, 1988, pp. 688-694.

Scharpenseel, H. W., "Direct tritium and carbon-14 labeling and liquid-scintillation spectrometry," Angewandte Chemie 71, 1959, pp. 640-646.

Scharpenseel, H. W., "Preparation and purification of gray and brown humic acid samples labeled with tritium and of tritium-pupurogallin," Zeitschrift fuer Pflanzenernaehrung, Duengung, Bodenkunde 91, 1960, pp. 131-146.

Scharpenseel, H. W., "Zur Herstellung von allseitig $C^{14}$-markiertem Pflanzen- und Huminsäurematerial (Production of Xandomly ($C^{14}$) labeled plant- and humic acid material," Landwirtschaftliche Forschung 14, 1961, pp. 42-48.

Schick, et al., "Synthesis of Tritium Labelled Phosphate Analogues of Sphinganine-1-Phosphate," Journal of Labelled Compounds and Radiopharmaceuticals 39(5), 1997, pp. 441-451.

Senesi, "Molecular and quantitative aspects of the chemistry of fulvic acid and its interactions with metal ions and organic chemicals, Part II. The fluorescence spectroscopy approach," Analytica Chimica Acta 23, 1990, pp. 77-106.

Slutzky, et al., "Identification of Galactose as the Immunodominant Sugar of Leishmanial Excreted Factor and Subsequent Labeling with Galactose Oxidase and Sodium Boro[$^3$H]hydride," Infection and Immunity 37(1), 1982, pp. 10-14.

Stevenson, "Reactive Functional Groups of Humic Substances," Humus Chemistry—Genesis, Composition, Reactions. New York, John Wiley & Sons, 1982, pp. 221-243.

Stumm, et al., "Aquatic Chemistry: Chemical Equilibria and Rates in Natural Waters," $3^{rd}$ ed., John Wiley & Sons, Inc.: New York, 1996; p. 301, p. 581.

Sutton et al., "Molecular Structure in Soil Humic Substances: The New View," Environmental Science & Technology 39, 2005, pp. 9009-9015.

Swift, Organic Matter Characterization (chap 35), 1996, In D.L. Sparks et al. (eds.) Methods of Soil Analysis, Part 3 Chemical Methods, Soil Sci. Soc. Am. Book Series: 5, Soil Sci. Soc. Am. Madison, WI, pp. 1018-1020.

Thorn, et al., "Covalent Binding of Aniline to Humic Substances. 2. $^{15}$N NMR Studies of Nucleophilic Addition Reactions," Environmental Science and Technology 30, 1996, pp. 2764-2775.

Thurman, "Humic Substances in Groundwater," Humic Substances in Soil, Sediment and Water, New York, John Wiley & Sons: 1985, pp. 87-103.

Tinnacher, et al., "A New Method to Radiolabel Fulvic Acids with Tritium for the Purpose of Tracing Organic Matter Transport at Low Concentrations," Poster presentation at $10^{th}$ International Conference on Chemistry and Migration Behavior of Actinides and Fission Products in the Geosphere, Migration 2005, Avignon, France, Sep. 18-23, 2005.

Tinnacher, et al., "A New Method to Radiolabel Fulvic Acids with Tritium," Poster presentation at the Graduate Student Association Research Fair, Colorado School of Mines, Apr. 5, 2006.

Tinnacher, et al., "A New Method to Radiolabel Natural Organic Matter by Chemical Reduction with Tritiated Sodium Borohydride," Environmental Science and Technology 41, 2007, pp. 6776-6782.

Wang et al., "Preparation of tritium-labeled fulvic acid (3H-FA)," Zhiwu Shenglixue Tongxun 6, 1984, pp. 42-44.

Wang et al., "The Fate of $^{14}$C-Labeled Humic Substances in Rice Cells in Culture," Journal of Plant Physiology 154(2), 1999, pp. 203-211.

Warwick et al., "The mobility and stability of iodine-humic and iodine-fulvic complexes through sand," The Science of the Total Environment 130/131, 1993, pp. 459-465.

Warwick, et al., "Carbon-14 and iodine-125 labelling of humic material for use in environmental studies," Chemistry and Ecology 8(2), 1993, pp. 65-80.

Warwick et al., "Radiolabelling of Humic Material by Enzymatically Mediated Incorporation of $^{14}$C-Phenol," Chemosphere 35(6), 1997, pp. 1161-1174.

Weber et al., "Covalent Binding of Aniline to Humic Substances. 1. Kinetic Studies," Environmental Science and Technology 30, 1996, pp. 2755-2763.

Wigfield et al., "Limited Alkoxy Group Exchange in Tetraalkoxyborohydrides: Evidence Against the Four-Centre Transition State in the Borohydride Reduction of Ketones," Tetrahedron Letters No. 38, 1976, pp. 3373-3376.

Wolf et al., "Migration behaviour of I-125 labelled aquatic fulvic acid from a peat bog," Isotope Techniques in the Study of Environmental Change, Vienna, International Atomic Energy Agency, 1997, pp. 888-892.

Wolfinbarger et al., "A Convenient Procedure for Radiolabeling Detritus with [$^{14}$C]Dimethylsulfate," J. Exp. Mar. Biol. Ecol. 67: 1983, pp. 185-198.

Yadav et al., Merits of sodium borohydride reductions under phase transfer catalysis—Part I, Outsourcing, CHIMICA OGGI/chemistry today, Jun. 2000, 6 pages.

Yan et al., "Gel Electrophoretic Quantitation of Protein Carbonyls Derivatized with Tritiated Sodium Borohydride," Analytical Biochemistry 265, 1998, pp. 176-182.

\* cited by examiner

| Method | Org. matter | Advantage(s) | Disadvantage(s) | Spec. activity |
|---|---|---|---|---|
| Methylation with [$^{14}$C]dimethylsulfate | Detrius, COM[b] | − Stable over wide pH range;<br>− Rapid method | − Pot. chemical alteration;<br>− Blocked react. gr. | 0.643 − 2.9 kBq mg$^{-1}$;<br>17.4 − 78 nCi mg$^{-1}$ |
| [$^{14}$C]methylamination | HA[c] | − Chem. stable label under mild cond.;<br>− Rapid method | − Pot. blocked/altered reactive groups;<br>− Unstable in the presence of clays | 70 − 1,400 kBq mg$^{-1}$;<br>2,000 − 38,000 nCi mg$^{-1}$ |
| Acetylation with [$^{14}$C]acetic anhydride | Detrius | − Stable covalent bond with label;<br>− Rapid method | − Primarily labels chitin, not cellulose;<br>− Charge alteration of primary amines | 9351 − 29,952 cpm mg$^{-1}$ [g] |
| Synthesis of [$^{14}$C] model compounds | Synth. FA[d], HA | − No changes in functionality;<br>− Stable, structurally incorporated radioisotope | − Considerably simplified overall structure and reactive group composition | 0.2 − 104 kBq mg$^{-1}$;<br>5 − 2,810 nCi mg$^{-1}$ |
| Enzymatic incorporation of [$^{14}$C]phenols | FA, HA | − Chem. stable label;<br>− Rapid method | − Pot. alteration of react. gr. conc. and arom. carb. content | 1.847 − 759 kBq mg$^{-1}$;<br>49.92 − 20,500 nCi mg$^{-1}$ |
| Biodegradation of [$^{14}$C] plant material | HA, LC[e] | − No changes in mol. structure;<br>− Stable, structurally incorporated label | − Time-consuming, complex exp. setup;<br>− Org. matter derived from a few plants | 0.02387 − 7.4 kBq mg$^{-1}$;<br>0.6450 − 200 nCi mg$^{-1}$ |
| Halogenation after oxidation of [$^{131}$I]I$^-$ by Iodogen | HM[f] | − Rapid, convenient method;<br>− Labeled over whole mol. size range | − Limited stability in daylight;<br>− Pot. blocking of reactive groups | appr. 10,000 kBq mg$^{-1}$;<br>appr. 270,270 nCi mg$^{-1}$ |
| [$^{125}$I]Iodination using chloramine-T as oxidizing agent | FA, HA | − Rapid method | − Stability limited during advective transport and chem. | 34 − 70.6 kBq mg$^{-1}$;<br>920 − 1,910 nCi mg$^{-1}$ |
| Indirect iodination with [$^{125}$I]Bolton-Hunter reag. | HM | − Rapid method | − Limited stability in the presence of sand | not reported |
| Enzymatic halogen ($^{131}$I, $^{36}$Cl) incorporation | HA | − Rapid method;<br>− Labeled over whole mol. size range | − Chemically unstable at high pH | not reported |
| Coupling with 4-[$^{18}$F]fluorobenzene-diazonium chloride | HA | − Chem. stable label over wide pH range;<br>− Rapid method | − Pot. unstable under reducing conditions;<br>− Pot. blocking of reactive groups | not reported |
| Reaction with reduced [$^{99m}$Tc]pertechnetate | HA | − Labeled over whole mol. size range | − Unspec. site location of label;<br>− Pot. blocking of reactive groups | not reported |
| Tritium ($^3$H) gas exchange (Wilzbach method) | HA | − Fairly representative labeled product | − Time-consuming, complex exp. setup;<br>− Partially unspec. site location of label | 10.26 − 26,700 kBq mg$^{-1}$;<br>277.2 − 722,000 nCi mg$^{-1}$ |

Figure 1

METHODS TO RADIOLABEL NATURAL ORGANIC MATTER BY REDUCTION WITH HYDROGEN LABELED REDUCING AGENTS

This application claims the benefit under 35 U.S.C. §119 (e) of U.S. Provisional Application No. 60/845,269, filed Sep. 15, 2006 and U.S. Provisional Application No. 60/845,842, filed Sep. 18, 2006, which are both incorporated by reference in their entirety.

The U.S. Government has a paid-up license in this invention and the right in limited circumstances to require the patent owner to license others on reasonable terms as provided for by the terms of Grant No. DE-FG 03-01 ER63242 awarded by the U.S. Dept. of Energy's Office of Science, Office of Biological and Environmental Research (BER), Natural and Accelerated Bioremediation Research (NABIR) Program (currently the Environmental Remediation Science Program (ERSP)).

FIELD OF THE DISCLOSURE

The disclosure relates to methods to radiolabel natural organic matter by reduction with tritiated borohydride.

BACKGROUND OF THE DISCLOSURE

Natural organic matter (NOM) plays an important role in numerous natural and engineered systems due to its ability to associate with metal ions and organic compounds in solution and to sorb to mineral and other surfaces (e.g. Stevenson, F. J. (1982). *Humus Chemistry—Genesis, Composition, Reactions*. New York, John Wiley & Sons.; Leenheer, J. A. and J. P. Croue (2003). "Characterizing aquatic dissolved organic matter." *Environmental Science & Technology* 37(1): 18A-26A.). Parameters and processes that are affected by the presence of NOM include the fate and transport of metals and organic contaminants in the environment, the environmental toxicity of organic and inorganic compounds, mineral weathering and metal leaching from soils, phytoremediation systems, scaling, and many more.

Humic substances represent an operationally defined, complex fraction of NOM with relatively high persistence in the environment due to their comparably low potential for microbial decomposition (MacCarthy, P. (2001). "The principles of humic substances." *Soil Science* 166(11): 738-751; Stevenson, F. J. (1982)). They are described as a heterogeneous mixture of natural polyelectric acids in soils and waters that cannot be further classified based on their chemical structure (Gaffney, J. S., N. A. Marley, et al. (1996). Humic and fulvic acids and organic colloidal materials in the environment. *Humic and Fulvic Acids: Isolation, Structure, and Environmental Role*. J. Gaffney, S., N. A. Marley and S. B. Clark. Washington, D.C., American Chemical Society: 2-16).

Unfortunately, for many systems of interest, the environmentally relevant concentration levels of natural organic ligands are so low that their straightforward analytical quantification in experimental investigations is hindered. For instance, typical concentration ranges of humic substances in groundwater have been reported between 0.04 to 8.6 mg $l^{-1}$ carbon (Thurman, E. M. (1985). Humic substances in groundwater. *Humic Substances in Soil, Sediment, and Water*. G. R. Aiken, D. M. McKnight, R. L. Wershaw and P. MacCarthy. New York, John Wiley & Sons: 87-103) and 0.1 to 10 mg $l^{-1}$ carbon (Gaffney et al., 1996). Conventional analytical techniques for NOM quantification, such as dissolved organic carbon (DOC) analysis, UV-absorbance and fluorescence, lack sufficient sensitivity and/or exhibit dependence on solution conditions and organic ligand speciation (Northcott, G. L. and K. C. Jones (2000). "Experimental approaches and analytical techniques for determining organic compound bound residues in soil and sediment." *Environmental Pollution* 108: 19-43; Novak, J. M., G. L. Mills, et al. (1992). "Estimating the percent aromatic carbon in soil and aquatic humic substances using ultraviolet absorbance spectrometry." *Journal of Environmental Quality* 21: 144-147; Senesi, N. (1990). "Molecular and quantitative aspects of the chemistry of fulvic acid and its interactions with metal ions and organic chemicals. Part II. The fluorescence spectroscopy approach." *Analytica Chimica Acta* 232: 77-106).

SUMMARY OF THE DISCLOSURE

The disclosure also provides methods of labeling natural organic matter (NOM) with tritium. NOM is first solubilized and insoluble NOM is removed to produce solubilized NOM. The solubilized NOM is treated with tritiated borohydride ($BH_4^-$), to label the solubilized NOM with tritium. The solubilized NOM comprises humic acid (HA) and fulvic acid (FA) in addition to other organic compounds with characteristic chemical structures. FA and HA typically have a ketone functionality, and/or aldehyde functionalities that are labeled with tritiated borohydride. They also contain quinones which are labeled but which produce relatively unstable chemical bonds with the label. To destabilize these and other unstable tritiated NOM products, the mixture can be aerated to reoxidize the unstable compounds, followed by an evaporation step that removes free tritium in solution.

The disclosure provides a method for labeling FA with tritium comprising contacting a solution of FA with tritiated borohydride to label the FA with tritium.

The disclosure also provides a method for labeling HA with tritium comprising contacting a solution of HA with tritiated borohydride to label the HA with tritium.

The methods produce novel tritiated NOM, HA, and FA.

The disclosure also provides methods for determining the concentration of natural organic matter (NOM). Solubilized NOM is labeled as above. The concentration of the NOM is then determined by measuring the radioactivity of the labeled NOM. In another aspect, the measured radioactivity is compared to the measured radioactivity of a tritiated NOM standard to determine the NOM concentration.

The disclosure also provides a method for determining the concentration of fulvic acid (FA) comprising tritiating solubilized FA as described and by measuring the radioactivity of the labeled FA to determine the concentration of FA. In another aspect, the measured radioactivity is compared to a measured radioactivity of a tritiated FA standard.

The disclosure also provides a method for determining the concentration of humic acid (HA) comprising tritiating solubilized HA as described by measuring the radioactivity of the labeled HA to determine the concentration of HA. In another aspect, the measured radioactivity is compared to a measured radioactivity of a tritiated HA standard.

The disclosure also provides methods of selecting a concentration of reducing agent for a desired labeling efficiency of a proton label in a composition. The concentration of a reducing agent is first compared to comparison data to determine the labeling efficiency and then the reducing agent is added to the composition. The comparison data can be in any representation, including a table, a chart, or a graph. Alternatively, the comparison data is prepared by deriving one or more equations correlating the concentration of functional groups of a NOM fraction with reducing agent concentration and labeling efficiency. The latter can be performed by following the modeling description provided herein.

BRIEF DESCRIPTION OF THE DRAWINGS

The following Figures represent exemplary embodiments of the disclosure and are not limiting.

FIG. 1 is an overview of currently available radiolabeling methods for humic substances and natural organic matter (NOM).

DETAILED DESCRIPTION OF THE DISCLOSURE

Figure 2:
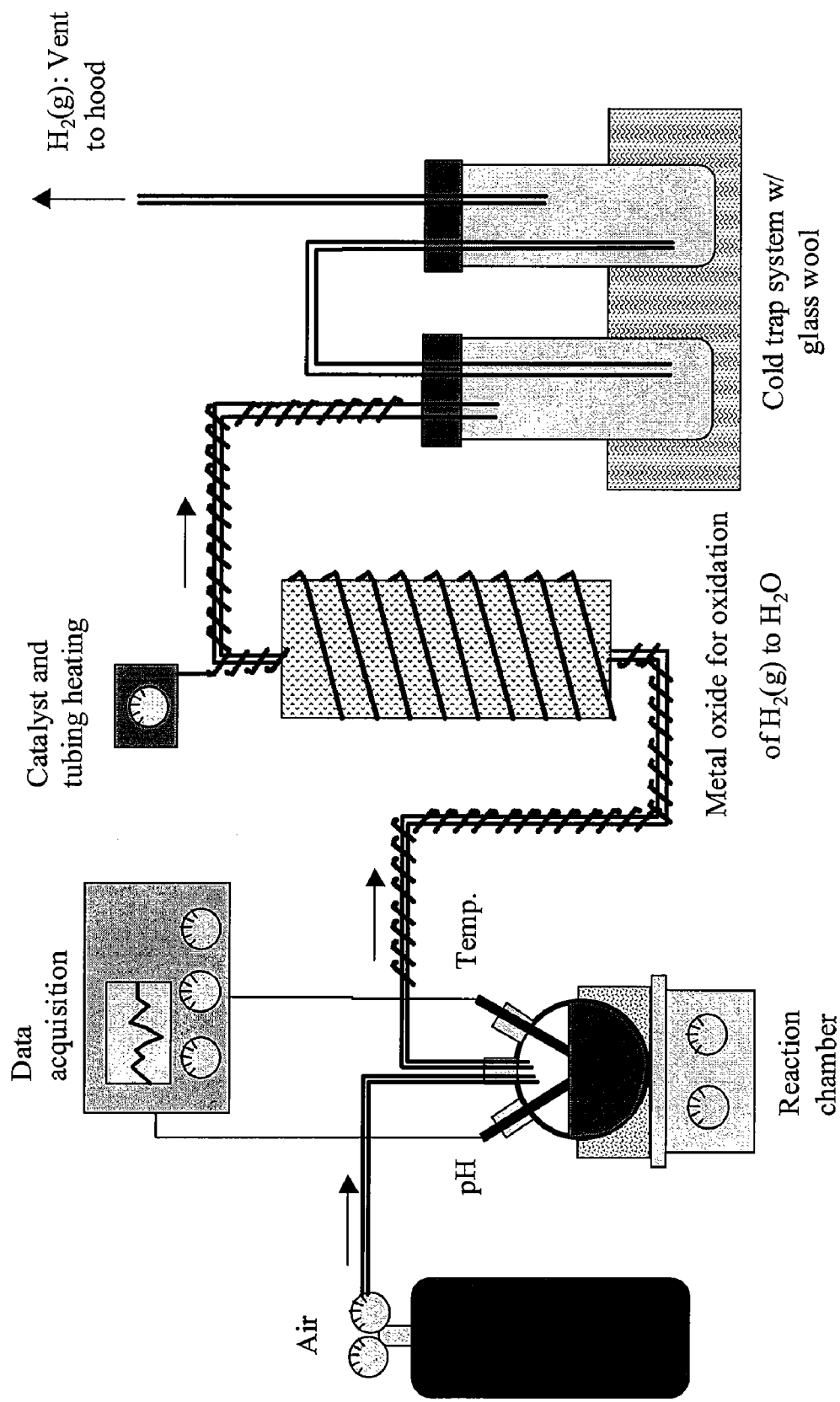
FIG. 2 is a schematic for the experimental setup for the labeling procedure.

The disclosure provides methods to radiolabel natural organic matter (NOM) with one of the hydrogen labels, deuterium (2H) and/or tritium (3H). The NOM is labeled using a reducing agent such as tritiated $NaBH_4$. Compositions of NOM are also provided.

Natural Organic Matter (NOM)

NOM is a very reactive, ubiquitous component in soil, sediment, water and air. It exerts a profound influence on many biophysico-chemical processes in the environment. For example, NOM exercises a vital role in soil quality and health by regulating the bioavailability and dynamic processes of metals, anthropogenic organic compounds and vital elements. NOM can be a major source of N, P, and S for plants, and a primary food and energy source that controls the ecological dynamics of soil and sediment biota. A better and more complete understanding of the formation, interactions with minerals, and turnover and storage of NOM and its biophysico-chemical roles in environmental systems is essential for the development of innovative management strategies for sustaining the environment. NOM are also precursors of some fossil fuels. They can also be found in peat, coal, many upland streams and ocean water.

As used herein, "natural organic matter (NOM)" is a complex mixture of carbon containing molecules derived from organic matter found in the environment. NOM can be obtained from the natural environment, such as from lakes, riverbeds, forests, peat, coal, upland streams, and ocean water. The carbon containing molecules of NOM are complex molecules varying from low to high molecular weights, including diagenetically altered biopolymers and black carbons. NOM can vary greatly depending on its origin, transformation mode, age, and existing environment. Thus, its biophysico-chemical functions and properties vary with different environments. NOM includes, but is not limited to, humic substances, which includes but is not limited to humin, humic acid (HA), and fulvic acid (FA). Besides humic substances, NOM also comprises organic compounds with defined chemical structures, e.g. polysaccharides, proteins, lignins and their derivatives.

As used herein, "humin" is the component of humic substances that is not water soluble.

As used herein "solubilized NOM" is any portion of NOM that is soluble in water. As used herein, solubilized NOM also includes fractions and derivatives of solubilized NOM that can be obtained by physical, chemical, or biological manipulation. Separation of solubilized NOM fractions can be obtained by physical manipulation, including but not limited to, chromotographic, such as by ion exchange chromatography, high performance liquid chromatography (HPLC), size exclusion chromatography, affinity chromatography, gas-liquid chromatography, countercurrent chromatography, as well as centrifugation. Derivatives of solubilized NOM can be obtained by chemical treatment that changes one or more chemical characteristics of solubilized NOM. Derivatives of solubilized NOM can also be obtained by biological manipulation of solubilized NOM, such as by treatment with, enzymes, microorganisms, etc.

As used herein, "fulvic acid" is that fraction of humic substances that is soluble in water at any pH.

As used herein, "humic acid" is that fraction of humic substances that is soluble in water within a limited pH region. At $pH \leq 2.0$, humic acids precipitate.

As used herein, "hydrogen label" or "proton label" is deuterium (2H) or tritium (3H).

As used herein, a "reducing agent" donates an electron to another compound, and includes, but is not limited to, $LiAlH_4$, $LiAl(OtBu)_3H$, $BH_4$ (e.g. $NaBH_4$ or $LiBH_4$), RMgX, Rli, RNa, $R_2CuLi$, $NH_2NH_2$.

In various embodiments, substantially equal molecular weight distribution means less than or equal to 30% variation in distribution of label (e.g. a $^2H$ or $^3H$ label) normalized to the molecular weight of each component in a mixture as measured by size exclusion chromatography. In other embodiments, the molecular weight distribution can be a less than or equal to 20%, 10%, or 5% variation in distribution of label normalized to the molecular weight of each component in a mixture as measured by size exclusion chromatography.

In various embodiments, substantially equal molecular size distribution means less than or equal to 30% variation in distribution of label (e.g. a $^2H$ or $^3H$ label) normalized to the molecular size of each component in a mixture as measured by size exclusion chromatography. In other embodiments, the molecular size distribution can be a less than or equal to 20%, 10%, or 5% variation in distribution of label normalized to the molecular size of each component in a mixture as measured by size exclusion chromatography.

As used herein, "substantially degrade" means more than 10% of $^2H$ or $^3H$ leaves a $^2H$ and/or $^3H$ labeled compound over a specific period of time.

As used herein, "substantial chemical degradation" means more than 10% of $^2H$ or $^3H$ leaves a 2H and/or $^3H$ labeled compound over specific period of time.

As used herein, "substantial isotope exchange" means more than 10% of 2H or 3H is exchanged between a NOM fraction and a solution.

Many different separation procedures are found for NOM and humic substances in the art and for samples from different environments (e.g. soil humics vs. aquatic humics). Various solvents can be used for the extraction, e.g. alkaline solutions or organic solvents. Precipitation at low pH is one option for the separation of humic and fulvic acids. Other techniques are possible as well, e.g. sorption of both fractions to a hydrophobic resin (XAD-8) followed by a two-step elution at pH=7 (fulvic acid) and with 0.1 N NaOH (humic acid).

Humic substances are a class of organic material occurring in, or extracted from, decayed or decaying biomatter in soil, sediment or natural waters, and that does not fall into any of the discrete classes of organic substances. Humic substances can only be defined by their source, extraction method, purification, and treatment method. The chemical nature of humic substances can be rationalized on the basis of the First Principle of Humic Substances. (MacCarthy, Patrick. The Principles of Humic Substances: An Introduction to the First Principle. In *Humic Substances Structures Models and Functions*; Elham A. Ghabbour, Geoffrey Davies, Eds.; Royal Society of Chemistry, 2001; pp. 19-30).

Humic substances are a complex, amorphous mixture of highly heterogeneous, chemically reactive yet refractory molecules, produced during early diagenesis in the decay of biomatter, and formed ubiquitously in the environment via processes involving chemical reaction of species randomly chosen from a pool of diverse molecules and through random chemical alteration of precursor molecules. Humic substances typically lack a regularly recurring, extended skeletal entity. Humic substances cannot be purified in the conventional meaning of purity. The essence of humic substances resides in the combination of their molecular heterogeneity and pronounced chemical reactivity. Humic substances from different sources display a remarkable uniformity in their gross properties. (MacCarthy, Patrick. The Principles of Humic Substances: An Introduction to the First Principle. *In Humic Substances Structures Models and Functions*; Elham A. Ghabbour, Geoffrey Davies, Eds.; Royal Society of Chemistry, 2001; pp. 19-30).

Humic substances are produced in the decay of biomatter in all terrestrial and aquatic environments throughout the world. The formation of humic substances occurs during early diagenesis of biomatter in contrast to the formation of coal and petroleum that are produced over geologic periods and under more severe metamorphic conditions. Materials that do not originate from the decay of biomatter in soil, sediment or natural waters should not be considered as humic substances even though they may display the same acid/base solubility behavior and color as humic substances.

Humic substances make up a large portion of the dark matter in humus and are complex colloidal supramolecular mixtures that have never been separated into pure components. Since the end of the 18th century, humic substances have been designated as either humic acid, fulvic acid or humin. These fractions are defined strictly on their solubility in either acid or alkali, describing the materials by operation only, thus imparting no chemical information about the extracted materials. The term humic substances is used in a generic sense to distinguish between NOM fractions with defined chemical structures (e.g. polysaccharides or proteins) and operationally defined complex mixtures of organic compounds that do not correspond to a unique chemical entity. Humic substances can be understood as those fractions of NOM that cannot be classified based on a specific chemical structure but contain a statistical distribution of chemical structures and characteristics. It is important to note, however, that no sharp divisions exist between humic acids, fulvic acids and humins. They are all part of an extremely heterogeneous supramolecular system and the differences between the subdivisions are due to variations in chemical composition, acidity, degree of hydrophobicity and self-associations of molecules. When humic substances are characterized, especially when functionality is studied, there is always the problem that one usually has to separate the huge number of different bioorganic molecules into slightly more homogenous fractions.

Humic substances arise by the microbial degradation of biomolecules (lipids, proteins, carbohydrates, lignin) dispersed in the environment after the death of living cells. A modern structural description regards humic material as a supramolecular structure of relatively small bio-organic molecules (having molecular mass<1000 Da) self-assembled mainly by weak dispersive forces such as van der Waals, $\pi$-$\pi$, and CH-$\pi$ bonds into only apparently large molecular sizes.

A large amount of humic molecules are represented by hydrophobic compounds (long alkyl-chain alkanes, alkenes, fatty acids, sterols, terpenoids, and phenyl-alkyl residues of lignin degradation) which allow their self-association into supramolecular structures separated from the water medium and, thus, their long residence time in the environment. Humic substances are endowed with acidic functional groups mainly carboxylic acid, which confer on these molecules the ability to chelate multivalent cations such as $Mg^{2+}$, $Ca^{2+}$, and $Fe^{2+}$. This chelation of ions is an important role of humic acids with respect to living systems. By chelating the ions, they facilitate the uptake of these ions by several mechanisms, one of which is preventing their precipitation, another seems to be a direct and positive influence on their bioavailability.

The present disclosure provides methods for radiolabeling of the soluble compounds of NOM. A number of methods for the extraction of humic substances from soil using sodium hydroxide solution have been published. See e.g., Swift, R. S. 1996 Organic matter characterization (chap 35). pp. 1018-1020. In D. L. Sparks et al. (eds.) *Methods of soil analysis. Part 3. Chemical methods*. Soil Sci. Soc. Am. Book Series: 5. Soil Sci. Soc. Am. Madison, Wis. The present disclosure provides in Example 11a method which has been developed by the International Humic Substance Society (IHSS) as one of many acceptable methods for the extraction of humic substances from soils.

Radiolabeling

Radiolabeling of organic ligands can provide a sensitive tool for the analysis of organic ligand concentrations over a range of experimental conditions. An overview of currently available radiolabeling techniques for humic and fulvic acids and NOM is provided in FIG. 1. Current methods are hampered by various chemical problems, e.g. the limited chemical stability of the label, and a lack of understanding regarding the underlying mechanisms of the labeling procedure. The latter prevents the successful prediction of the specific activity of radiolabeled products in new method applications. Labeling methods accomplish one or more of the following:

1) The long-term chemical stability of the labeled product over a wide range of system conditions (e.g., pH, $E_h$);

2) High specific activities of the labeled product;

3) Minimal alteration, addition or blocking of reactive groups relevant for the reactions of humics with metals and organic compounds in solution and to various surfaces;

4) The ability to preserve the intrinsic, complex nature of humic substances;

5) A detailed understanding of the chemical mechanisms involved in the labeling reaction;

6) A detailed chemical characterization of the labeled product and its physico-chemical differences relative to the original material;

7) A model that predicts the labeling efficiency and specific activity of the product when the method is applied to other fractions of organic matter.

The chemical stability of the labeled product is essential to avoid potential errors in the analytical quantification of radiolabeled organic matter in later experiments, which could lead to serious misinterpretations of experimental results. Unfortunately, the lack of chemical stability is the major limiting factor for several currently available radiolabeling techniques. Further, sufficiently high specific activities are needed to ensure that radiolabeled NOM provides a sensitive and useful analytical tool; ideally, the labeled product is used as a tracer material in later experiments. Any potential changes in relevant reactive group concentrations and composition need to be minimized and the complex nature of NOM, e.g., molecular weight and size distribution, preserved to ensure that the radiolabeled compounds are still representative for natural organic matter. The latter excludes the use of synthetic "humic-like" compounds, which cannot resemble natural organic matter in its full complexity. In addition, a detailed understanding of the chemical mechanisms involved in the labeling reaction followed by a chemical characterization of the labeled product is necessary. This ensures that potential limitations of the radiolabeling method are well understood and can be evaluated prior to its use in specific applications. The use of a predictive model describing labeling efficiencies and specific activities of the product will allow for the tailoring of the method to new applications. Other organic matter fractions containing known concentrations of reactive groups suitable for the reduction with $NaBH_4$ can then be labeled without additional experimental testing.

Chemical Background of Deuterium and/or Tritium Labeling

The present disclosure provides a method to produce radiolabeled natural organic matter (NOM), such as humic acid and fulvic acids, with tritium.

In one embodiment, humic and/or fulvic acid is labeled with tritium by the chemical reduction of ketones and/or aldehydes with tritiated sodium borohydride ($NaBH_4$).

The use of tritium as ancillary tracer for organic molecules has numerous advantages. Tritium is readily available in high quantities, and high specific activities of labeled compounds are produced which can be conveniently quantified by liquid scintillation counting. Further, tritium half-life (12.26 years) is sufficiently long, its biological half-life short, and tritium toxicity is listed in the lowest class of radioactive materials (Evans, A. E. *Tritium and its compounds*; Butterworth & Co. Ltd.: Princeton, N.J., Toronto, London, N.Y., 1966; Chapter 1-3). However, the successful application of tritium labeled compounds depends on sufficient knowledge of the integrity of the carbon-hydrogen bond under various chemical conditions.

The present disclosure provides a method, wherein humic and/or fulvic acid (FA) are labeled with a hydrogen label, such as deuterium or tritium, by chemical reduction with a deuterated or tritiated reducing agent, such as sodium borohydride ($NaBH_4$). FA carbonyl groups of aliphatic and aromatic ketones as well as quinones are selectively reduced to yield secondary alcohols and hydroquinones/phenols, respectively. This reduction is a two-step process based on the following reaction (McMurry, J. *Organic Chemistry*, 5$^{th}$ ed., Brooks/Cole: Pacific Grove, Calif., 2000; pp. 768-769).

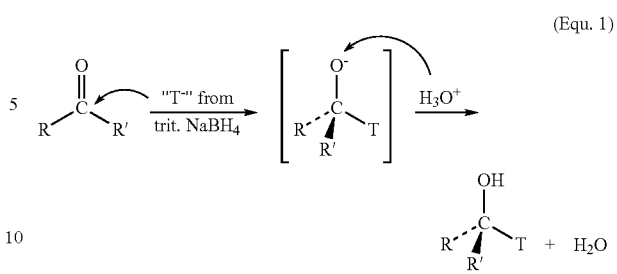

(Equ. 1)

Suitable functional groups are reduced by adding a reducing agent such as $NaBH_4$. The first step is a nucleophilic addition reaction, where $NaBH_4$ acts as a donor of a hydride ion that is attracted to the partial positive charge of the carbonyl carbon. In the second step, water protonates the tetrahedral alkoxide intermediate and gives the alcohol product. In the case of a reaction with tritiated $NaBH_4$, at the most one tritium atom (T) can be bound to one carbon per carbonyl group reduction. Since the proton forming the secondary alcohol originates from water, the stability of the tritium label is not affected by the dissociation of alcohols and the labeled product can be assumed to be chemically stable over the whole pH range. Furthermore, the covalent carbon-tritium bond is expected to be stable under both oxidizing and reducing conditions, as the oxidation of alcohols by dissolved oxygen is a slow process, and reducing conditions should not have any significant effects on the products of a reduction reaction.

While FA carbonyl groups of both ketones and quinones are selectively reduced in this example, the reduction products of quinones are not expected to be stable in aerobic environments over time. Literature suggests that FA hydroquinones formed by $NaBH_4$ reduction can be reoxidized in reactions with molecular oxygen or by intramolecular redox processes (Thorn, K. A.; Pettigrew, P. J.; Goldenberg, W. S.; Weber, E. J. *Environ. Sci. Technol.* 1996, 30, 2764-2775; Weber, E. J.; Spidle, D. L.; Thorn, K. A. *Environ. Sci. Technol.* 1996, 30, 2755-2763). Since these reactions would lead to free T$^+$ in solution, this could result in large analytical errors associated with the quantification of radiolabeled organic matter concentrations. Therefore, as part of the radiolabeling procedure, an aeration step is performed, after completion of the reduction reaction, to reoxidize unstable products under controlled experimental conditions. Afterwards, the water contained in the reaction vessel is completely evaporated for the removal of T$^+$ in solution.

FA contains various types of functional groups. Carboxyl and phenol groups are assumed to play the major role in FA metal complexation reactions, and aromatic and aliphatic moieties contribute to the hydrophobic properties of FA, which affect its accumulation on the solid water interface (Stumm, W., Morgan, J. J. *Aquatic chemistry: chemical equilibria and rates in natural waters,* 31$^{rd}$ ed., John Wiley & Sons, Inc.: New York, 1996; pp. 301, pp. 581). While ketones may also be involved in metal complexation reactions, they only represent weak complexing sites compared to carboxyl and phenol groups. Therefore, the consumption of HA or FA carbonyl groups during labeling allows us to minimize adverse alterations of the chemical behavior of HA or FA. Carbonyl groups may be of importance, however, for the investigation of the covalent binding of aniline to humic substances (Thorn et al., 1996; Weber et al., 1996), the photoproduction of carbonyl sulfide and carbon monoxide from dissolved organic matter (Pos, W. H.; Riemer D. D.; Zika, R. G.

Marine Chemistry 1998, 62, 89-101), and in direct studies of humic ketone groups (Leenheer, J. A.; Wilson, M. A.; Malcolm R. L. Org. Geochem. 1987, 11, 4, 273-280). Furthermore, the production of additional alcoholic groups during labeling will render the organic matter slightly more hydrophilic.

Various reagents can be used for the chemical reduction reaction. Any reducing agent as described herein can be used. In certain preferred embodiments, $NaBH_4$ is chosen because of its safety and ease of handling. Sodium borohydride is a white, crystalline solid that can be weighed in the open atmosphere and used in either water or alcohol solutions. High yields of products are usually obtained in reduction reactions with $NaBH_4$, which has made this compound the primary reductant used for organic synthesis on the industrial scale (Rohm and Haas, The Sodium Borohydride Digest, 2003, http://www.hydridesolutions.com/technical.html#). Furthermore, considerable information is available on reaction mechanisms and products (Gaylord, N. G. Reduction with complex metal hydrides; Interscience Publishers, Inc:, New York, 1956; Chapter 2, 3, 6, 7; Periasamy, M.; Thirumalaikumar, M. Journal of Organometallic Chemistry 2000, 609, 137-151; Wigfield, D.C.; Gowland, F. W. Tetrahedron Letters 1976, 38, 3373-3376; McMurry, J.; Castellion, M. E. Fundamentals of Organic and Biological Chemistry, $2^{nd}$ ed., Prentice-Hall, Inc.: Upper Saddle River, N.J., 1999; pp. 141-144; Rohm and Haas, 2003), as well as on examples of successful reductions of humic substances with $NaBH_4$ (Stevenson, 1982; Thorn et al., 1996; Weber et al., 1996; Pos et al., 1998; Leenheer et al., 1987).

Tritiated $NaBH_4$ is usually prepared by direct exchange with tritium gas, wherein, based on simple calculations, the large portion of tritiated molecules contains only one tritium atom (Evans, 1966). This is relevant for the estimation of the specific activity of the labeled product. Tritiated $NaBH_4$ does not exchange tritium upon dissolution in water or alkali (Evans, 1966), and numerous examples of successful tritium labeling of other organic compounds with $NaBH_4$ are available in literature (e.g., Lenz, A.-G.; Costabel, U.; Shaltiel, S.; Levine, R. L. Analytical Biochemistry, 1989, 177, 419-425; Ichinose, K.; Leeper, F. J.; Battersby, A. R. Journal of the Chemical Society, Perkin Transactions 1: Organic and Bio-Organic Chemistry (1972-1999) 1993, 11, 1213-1216). Tritiated $NaBH_4$, however, can be decomposed in neutral and acidic aquatic solutions leading to the production of tritiated hydrogen gas (Rohm and Haas, 2003).

$$NaBH_4 + 4H_2O \rightarrow NaB(OH)_4 + 4H_2 \quad \text{(Equ. 2)}$$

Sodium borohydride degradation can be minimized by the optimization of solution parameters, such as pH and temperature (Rohm and Haas, 2003). For that reason, the labeling reaction is performed at high solution pH and at two temperature levels. However, additional safety measures are included in the labeling procedure to avoid the potential exposure to tritium gas.

Labeling

The present disclosure provides a method to label NOM, such as Suwannee River fulvic acid (FA) at a high specific activity e.g., 1.89 mCi $mg^{-1}$ FA. During this reduction reaction with tritiated sodium borohydride, ketone groups are transformed into secondary alcohols, while carboxyl and phenol groups are not affected. Labeling efficiency experiments determined that at least a ten-fold molar excess concentration of $NaBH_4$ is needed for optimum reduction conditions.

After the efficiency of the labeling reaction is optimized in experiments, the efficiency data are used to develop models that allow for the tailoring of this method to other organic compounds. The labeled product is characterized in terms of its specific activity and chemical characteristics by liquid scintillation counting, FTIR and NMR spectroscopy, and size exclusion chromatography. Batch sorption experiments are used to draw a comparison between the sorption characteristics of labeled and original fulvic acid. In addition, these sorption experiments also test the chemical stability of the label over a wide pH range and in the presence of a mineral surface.

The comparison of FTIR spectra of untreated and cold-labeled FA showed that relevant chemical characteristics, such as carboxyl group functionality were preserved during labeling, and excluded any potential boric acid contamination. The analysis of $^1H$-NMR spectra of FA before and after labeling confirmed the described reaction mechanism, but also revealed the potential for small methanol impurities in labeled samples. Last but not least, the sorption characteristics of radiolabeled FA to hematite were in good agreement with the sorption behavior of the original FA sample. In conclusion, this is a robust method to produce chemically stable, radiolabeled FA for the use as tracer at low concentration levels (detection limit: 0.3 μg $l^{-1}$ FA).

Modeling

The present disclosure also provides chemical and mathematical labeling efficiency models that are used for the tailored application of the present disclosure for the preparation of various radiolabeled compounds at various specific activities.

The present disclosure also provides methods of selecting a concentration of reducing agent for a desired labeling efficiency of a proton label in a composition. The concentration of a reducing agent is first compared to comparison data to determine the labeling efficiency and then the reducing agent is added to the composition. The comparison data can be in any representation, including a table, a chart, or a graph. Alternatively, the comparison data is prepared by deriving one or more equations correlating the concentration of functional groups of a NOM fraction with reducing agent concentration and labeling efficiency. The latter can be performed by following the modeling description provided herein.

Model parameters are determined by fitting mathematical expressions to the experimental absorbance curve, which consists of solution absorbance at 465 nm (ABS) versus molar $NaBH_4$ excess concentrations (x). Other chemical and/or non-chemical parameters known in the art can be used to indicate or determine reduction efficiency, for example measurements based on NMR or FTIR spectroscopy, or gas and/or liquid chromatography. The present disclosure provides in total, three models, one mathematical and two chemical.

The mathematical model is used as a reference to compare its goodness-of-fit estimate with the fits of chemical models, and is not intended to represent any specific chemical aspects of the system. It is based on the assumption that the absorbance curve can be fit with the following equation (e.g., using Mathematica, 4.1).

$$ABS = a_1 + b_1 exp(-c_1 x) \quad \text{(Equ. 3)}$$

The molar $NaBH_4$ excess concentration in solution (x) is defined as $$x = \frac{[NaBH_{4,Tot}]}{[FA_{Tot}]} \quad \text{(Equ. 4)}$$

with [NaBH$_{4,Tot}$] ... total concentration of NaBH$_4$ in solution,

[FA$_{Tot}$] ... total reactive group concentration of fulvic acid (FA) in solution.

In both chemical models, the absorbance curve was fit with equations that are based on chemical principles, such as the mass action expression of the labeling reaction, the mass balance equations for FA-reactive groups and NaBH$_4$ in solution and a number of additional assumptions. The set of equations for both chemical models is the same, except for the way in which the FA-reactive groups are parameterized. In chemical model #1, the FA-reactive group concentration is set at a fixed value (2.6 mmol g$^{-1}$ FA), which is the total number of aromatic and aliphatic ketone groups of Suwannee River fulvic acid (Averett, R. C. Leenheer, J. A., McKnight, D. M., Thorn, K. A. 1994. Humic Substances in the Suwannee River, Ga.: Interactions, Properties, and Proposed Structures, USGS Water-Supply Paper 2373). The reactions of FA-quinones are neglected due to the fact that their concentration is reported to be orders of magnitude lower than that for ketones (Averett et al., 1994; Ratasuk, N. (2004). *Redox functional groups of humic substance*. Ph.D. Dissertation, School of Civil Engineering and Environmental Science, University of Oklahoma). With chemical model #2, however, we test if the model fit can be further improved if a variation of the FA-reactive group concentration is allowed during fitting by including an additional fitting parameter.

In the following, the mathematical backbone of chemical model #1 is derived and the differences between the two chemical models are explained. The assumptions and definitions for chemical model #1 are summarized in the following:

(1) The reduction of aromatic and aliphatic FA-ketones (FA-Ket) can be simplified to the following reaction and mass action expression:

(Equ. 5)

with FA–Ket$_{Ox}$, FA–Ket$_{Red}$ oxidized or reduced ketone groups of FA

NaBH$_{4,Ox}$, NaBH$_{4,Red}$ ... oxidized or reduced forms of NaBH$_4$ and $$K = \frac{[FA - Ket_{Red}][NaBH_{4,Ox}]}{[FA - Ket_{Ox}][NaBH_{4,Red}]} \quad \text{(Equ. 6)}$$

(2) There is a linear relationship between the measured light absorbance of the reaction solution at equilibrium and the reduction efficiency: light absorbance (ABS) decreases with increasing efficiency (E):

$$E = -k \times ABS + d \quad \text{(Equ. 7)}$$

$$ABS = -\frac{E-d}{k} = \frac{d}{k} - \frac{E}{k} \quad \text{(Equ. 8)}$$

To simplify equation 8, we define a=1/k, which gives $$ABS = a(d-E) \quad \text{(Equ. 9)}$$

For now, we further assume that the light absorbance of the reaction solutions that contained zero and the maximum concentration of NaBH$_4$ reflect minimum and maximum efficiency values of E=0 and E=1, respectively. Based on this assumption, we determine estimates for the parameters a and d from equation 9, which are then used as starting values in numerical simulations.

(3) The reduction efficiency is defined as the concentration ratio of reduced to total FA-ketone groups:

$$E = \frac{[FA - Ket_{Red}]}{[FA - Ket_{Tot}]} = 1 - \frac{[FA - Ket_{Ox}]}{[FA - Ket_{Tot}]} \quad \text{(Equ. 10)}$$

(4) One mole of FA-ketones is reduced with one mole of sodium borohydride. Therefore, for the reaction products it follows that $$[FA-Ket_{Red}] = [NaBH_{4,Ox}] \quad \text{(Equ. 11)}$$

(5) Reduction reactions of NaBH$_4$ with any other potentially reactive groups of FA, e.g., quinones, are assumed to be negligible based on their significantly lower concentration (Averett et al., 1994; Ratasuk, 2004).

(6) The mass balance equations for FA-ketones and NaBH$_4$ in solution are defined as follows:

$$[FA-Ket_{Tot}] = [FA-Ket_{Ox}] + [FA-Ket_{Red}] \text{ and} \quad \text{(Equ. 12a)}$$

$$[FA-Ket_{Ox}] = [FA-Ket_{Tot}] - [FA-Ket_{Red}] \quad \text{(Equ. 12b)}$$

$$[NaBH_{4,Tot}] = [NaBH_{4,Ox}] + [NaBH_{4,Red}] \text{ and} \quad \text{(Equ. 13a)}$$

$$[NaBH_{4,Red}] = [NaBH_{4,Tot}] - [NaBH_{4,Ox}] \quad \text{(Equ. 13b)}$$

with

[FA-Ket$_{Tot}$], [FA-Ket$_{Ox}$], [FA-Ket$_{Red}$] ... molar concentrations of total, oxidized and reduced FA-ketone groups; [NaBH$_{4,Tot}$], [NaBH$_{4,Ox}$], [NaBH$_{4,Red}$] ... molar concentrations of total, oxidized and reduced forms of NaBH$_4$.

During the mathematical derivation of chemical model #1, an expression for the reduction efficiency (E) was derived to link E to the chemical equations stated above. Then, this expression was substituted into the linear relationship between light absorbance and reduction efficiency (Equ. 9).

At the beginning of the derivation of E, the expressions for [FA-Ket$_{Ox}$] (Equ. 12b) and [NaBH$_{4,Red}$] (Equ. 13b) originating from the mass balance equations were substituted in the mass action expression K (Equ. 6), so that $$K = \frac{[FA - Ket_{Red}]}{[FA - Ket_{Tot}] - [FA - Ket_{Red}]} \times \frac{[NaBH_{4,Ox}]}{[NaBH_{4,Tot}] - [NaBH_{4,Ox}]} \quad \text{(Equ. 14)}$$

Then, the assumption that [FA-Ket$_{Red}$]=[NaBH$_{4,Ox}$] (Equ. 11) is included and all terms are divided by [FA-Ket$_{Tot}$]$^2$, which leads to $$K = \frac{\left(\frac{[FA - Ket_{Red}]}{[FA - Ket_{Tot}]}\right)^2}{\frac{[NaBH_{4,Tot}]}{[FA - Ket_{Tot}]} - \frac{[FA - Ket_{Red}] \times \{[NaBH_{4,Tot}] + [FA - Ket_{Tot}]\}}{[FA - Ket_{Tot}]^2} + \frac{[FA - Ket_{Red}]^2}{[FA - Ket_{Tot}]^2}} \quad \text{(Equ. 15)}$$

Further, we used the definition for the reduction efficiency (Equ. 10) to express the equation in terms of E:

$$E^2(K-1) - E\left\{K\left(\frac{[NaBH_{4,Tot}]}{[FA-Ket_{Tot}]} + 1\right)\right\} + K\frac{[NaBH_{4,Tot}]}{[FA-Ket_{Tot}]} = 0 \quad \text{(Equ. 16)}$$

With the definition of excess $$NaBH_4, \ x = \frac{[NaBH_{4,Tot}]}{[FA-Ket_{Tot}]},$$

the equation further simplifies to $$E^2(K-1) - E\{K(x+1)\} + Kx = 0 \quad \text{(Equ. 17)}$$

which has the following two solutions:

$$E_{1,2} = \frac{K(x+1) \pm \sqrt{\{K(x+1)\}^2 - 4(K-1)Kx}}{2(K-1)} \quad \text{(Equ. 18)}$$

We determined the correct solution for E by using the following condition: for $$[NaBH_{4,Tot}] = 0 \ \text{and} \ x = \frac{[NaBH_{4,Tot}]}{[FA-Ket_{Tot}]} = 0$$

the valid efficiency value is E=0. Therefore, we find $E_2$ (negative sign) as solution, substitute this expression into the absorbance definition (Equ. 9), and further simplify the equation by defining $$b = \frac{K}{K-1}:$$

$$ABS = ad - \frac{ab}{2}(x+1) + a\sqrt{\frac{b^2}{4}(x+1)^2 - bx} \quad \text{(Equ. 19)}$$

Last, we implement the following parameters to simplify the numerical fitting process.

$$\beta_0 = ad \quad \text{(Equ. 20-23)}$$
$$\beta_1 = \frac{ab}{2}$$
$$\gamma_1 = \frac{4}{b}$$
$$z_1 = x + 1$$

The resulting equation is used for the fitting of the absorbance data for chemical model #1 (Mathematica 4.1).

$$ABS = \beta_0 - \beta_1\{z_1 - \sqrt{z_1^2 - \gamma_1(z_1-1)}\} \quad \text{(Equ. 24)}$$

In chemical model #2, however, we allowed for the additional fitting of the FA-reactive group concentration using the following equation:

$$[FA]_{React,Tot} = \alpha_0[FA-Ket]_{Tot} \quad \text{(Equ. 25)}$$

$[FA]_{React, Tot}$ . . . . Total, molar concentration of FA-reactive groups
$[FA-Ket]_{Tot}$ . . . . Total molar concentration of FA-ketone groups
$\alpha_0$ . . . Coefficient and fitting parameter This fitting can lead to three possible results for $\alpha_0$. First, if $\alpha_0=1$, the concentration of FA-reactive groups is equal to the total concentration of FA-ketones. Second, if $\alpha_0<1$, the FA-reactive group concentration is less, which implies that not all FA-ketone groups are accessible during the reduction with $NaBH_4$. Third, with $\alpha_0>1$, the concentration of FA-reactive groups is greater, and additional FA-functional groups may indeed be relevant for the reaction. Using a slightly modified nomenclature, chemical model #2 describes the simplified reduction reaction of FA-reactive groups and the correlated mass action expression as $$FA_{Ox} + NaBH_{4,Red} \rightleftharpoons FA_{Red} + NaBH_{4,Ox} \quad \text{(Equ. 26)}$$

with $FA_{Ox}$, $FA_{Red}$ . . . oxidized or reduced FA-reactive groups
$NaBH_{4,Ox}$, $NaBH_{4,Red}$ . . . oxidized or reduced form of $NaBH_4$ and

$$K = \frac{[FA]_{Red}[NaBH_{4,Ox}]}{[FA]_{Ox}[NaBH_{4,Red}]} \quad \text{(Equ. 27)}$$

Further, the mass balance equation for FA-reactive groups is now defined as $$[FA]_{React,Tot} = \alpha_0[FA-Ket]_{Tot} = [FA]_{Ox} + [FA]_{Red} \ \text{with} \quad \text{(Equ. 28a)}$$

$$[FA]_{Ox} = \alpha_0[FA-Ket]_{Tot} - [FA]_{Red} \quad \text{(Equ. 28b)}$$

and the efficiency of the reduction reaction (E) is expressed in terms of $$E = \frac{[FA]_{Red}}{[FA]_{React,Tot}} = \frac{[FA]_{Red}}{\alpha_0[FA-Ket]_{Tot}}. \quad \text{(Equ. 29)}$$

When we follow a similar mathematical derivation as for chemical model #1, and include the simplifying parameters from equations 20-23, as well as $$\alpha = \frac{1}{\alpha_0}, \quad \text{(Equ. 30)}$$

this results in the following expression for the light absorbance (ABS):

$$ABS = \beta_0 - \beta_1\{1 + \alpha x - \sqrt{(\alpha x+1)^2 - \alpha\gamma_1 x}\} \quad \text{(Equ. 31)}$$

This equation is used to fit the absorbance curve for chemical model #2.

The present disclosure provides a method for labeling a fulvic acid composition with a hydrogen label. In certain preferred embodiments, the hydrogen label is tritium ($^3H$). In other embodiments, the label is distributed substantially equally by molecular weight in the fulvic acids. In other words, there can be less than or equal to a 30% variation in distribution of the label (e.g. a $^2H$ or $^3H$ label) normalized to the molecular weight of each component in a mixture, as measured by size exclusion chromatography. In other embodiments, the molecular weight distribution can be less than or equal to 20%, 10%, or 5% variation in distribution of the label normalized to the molecular weight of each component in a mixture as measured by size exclusion chromatography.

Applications

The present disclosure also provides methods for analyzing the parameters and processes that are affected by the presence of NOM including, but not limited to fate and transport of metals and organic contaminants in the environment, the environmental toxicity of organic and inorganic compounds, mineral weathering and metal leaching from soils, phytoremediation systems, and scaling.

By "environmental toxicity" herein is meant being toxic to the environment or a component of it, such as being toxic to humans, animals, plants, or other living organisms.

By "mineral weathering" herein is meant the release of base cations from mineral dissolution.

By "leaching" herein meant is the process of extracting a substance from a solid by dissolving it in a liquid. Leaching is an environmental concern when it contributes to groundwater contamination. As water, from rain, flooding or other sources, seeps into the ground, it can dissolve chemicals and carry them into the underground water supply. Of particular concern are hazardous waste dumps and landfills, and, in agriculture, excess fertilizer and improperly stored animal manure. Metal leaching is the process of extracting metal from soil by liquid, such as water resulted from rain or flooding.

By "phytoremediation" herein is meant the treatment of environmental problems through the use of plants.

By "scaling" herein is meant the process of removing scale(s), as from metal.

All the references cited herein are expressly incorporated in their entirety by reference.

EXAMPLES

Example 1

Reagents

All solutions used in labeling experiments were prepared with autoclaved UV-water (Barnstead EASYpure UV compact ultrapure water system, Tuttnauer Brinkmann 3870 M autoclave). Suwannee River Reference fulvic acid in the hydrogen form (International Humic Substances Society, Cat. No. 1 R101F-1) was selected for radiolabeling as it represents a well-characterized, commonly available humic material. Tritiated sodium borohydride (7.6 mg $NaBH_4$, 100 mCi of 500 mCi/mmol) was purchased from ARC, American Radiolabeled Chemicals, Inc. (ART 121, Lot No. 041123), and non-radioactive $NaBH_4$ powder from Fisher Scientific (25 g, >98% purity, S678-25). Fulvic acid (FA) and tritiated $NaBH_4$ were stored frozen; non-radioactive $NaBH_4$ was stored in a desiccator prior to use.

A cation exchange resin (Biorad AG MP-50, analytical grade, 100-200 mesh, cation exchange capacity: 1.5 meq $ml^{-1}$ (moist), 3.5 meq $g^{-1}$ (dry)) in the hydrogen form was used in the first $NaBH_4$ cleanup step after preconditioning of the resin in the following manner: Resin (25 g) was packed as slurry into two glass columns, fed with 100 ml UV-water for the removal of fines, and treated with 100 ml of about 10% hydrochloric acid. Then, the resin beds were rinsed with UV-water (at least 900 ml in 100 ml batches) until the pH of the effluent stabilized at the original value. The preconditioned resin was partially air-dried and stored airtight. This resin material was selected due to its previous successful use with humic substances (Aiken, G. R.; McKnight, D. M.; Thorn, K. A.; Thurman, E. M. *Org. Geochem.* 1992, 18, 4, 567-573).

Example 2

Experimental Setup for Labeling Reaction

All relevant steps of the labeling experiments were performed in hoods. Glassware in contact with FA was acid and base washed (10% (v/v) HCl, 1% (w/v) NaOH) and autoclaved (Tuttnauer Brinkmann 3870 M autoclave).

A gastight, roundflask (50 mL, three-neck 19/22, Kemtech America: F439950) was set up as a reaction vessel in a water bath at 60° C. on a Corning stirrer/hotplate (FIG. 2). The openings of the flask were used to insert a small pH probe (VWR Scientific: Cat. No.: 34105-021), a thermocouple (Pasco Scientific CI-6505 temperature sensor), and a gastight glass addition funnel with stopcock (14/20 joint, ACE glass: 7257/9498), and to provide the gas in - and outlets (Masterflex tubing through greased rubber stoppers). The signal of the pH probe was amplified using a Pasco Scientific-C16507 pH electrode amplifier. The amplifier and the thermocouple were connected to a laptop computer over a Pasco Scientific/Science Workshop 500 interface to record and monitor pH and temperature over the course of the experiment (Science Workshop 2.2.5 data acquisition program).

Tritiated hydrogen gas, potentially produced by $NaBH_4$ decomposition, was continuously removed from the gastight reaction vessel to avoid explosive mixtures of $H_2$ (g) (LFL=4% $H_2$ (g)). For that purpose, a regulated flow of zero-grade-air was supplied from a gas cylinder to the gas inlet of the reaction vessel (General air cylinder: CGA590, Masterflex tubing 06419-16, Matheson 600 tube cube flow regulator). The off-gas was lead from the reaction vessel through heat-resistant tubing (Masterflex platinum-cured silicone 3350 tubing, 96420-16) to a stainless-steel column (1 ft. long, ¾ in.×0.065 in. wall tubing, Denver Valve & Fitting Co.: SS-T12-S-065-20) for off-gas treatment. This column was packed with a platinum catalyst bed (platinum on ⅛-inch alumina pellets, 0.5% Pt, 25 g, ACROS Organics: 19530 0250) to promote the oxidation of tritiated $H_2$ (g) to tritiated water vapor. In order to avoid the condensation of tritiated water inside the tubing and the catalyst bed, the steel column and the tubing were wrapped with a flexible small-diameter fiberglass heating cord (Cole-Parmer: U-03122-6) and continuously heated (Variac SE Powerstat Variable Transformer: 3PN 116B). A thermocouple (TE Omega, type K) was packed inside the catalyst bed and connected to a handheld digital thermometer (Omega HH-25KC) to allow for manual temperature monitoring and control. The temperature of the catalyst bed was held at 115° C. or higher at all times during the experiment.

The design of the catalyst system was based on the worst-case scenario: the complete decomposition of $NaBH_4$ into hydrogen gas over a short timeframe (40 min.). The flow rate of zero-grade air was set in such a way (58.8 ml $min.^{-1}$) that the highest expected hydrogen concentration could still be diluted to concentration levels (<2.5% $H_2$ (g)) that can be completely oxidized on the Pt-catalyst. The air-tightness of the setup and the efficiency of hydrogen oxidation on the catalyst surface was tested by injection of various (non-radioactive) $H_2$ (g)-air mixtures into the heated catalyst bed while the hydrogen content in the off-gas was monitored with a hand-held $H_2$ (g) detector (TIF 8800 permissible gas detector; $H_2$ (g) detection limit: 500 ppm). These experiments successfully demonstrated that $H_2$ (g) concentrations of up to 7.2% can be efficiently removed from the off-gas under the specified conditions (data not reported), and ensured a gastight system.

For the final collection of the tritiated water vapor, the top of the catalyst column was connected to a cooling trap with heated glass tubing. The cooling trap consists of two glass culture tubes (approx. O.D.=25 mm, length=250 mm, Kimble Art. No.:45048-25250), connected in series via bend glass-tubing, and submersed into ice-water in a dewer. In these tubes, tritiated water vapor is condensed over heat-resistant glass wool (Shimadzu: P/N: 630-00557-00). Finally, the off-gas of the cooling trap was monitored for $H_2$ (g) with the handheld detector described above, and released into the atmosphere of the radioisotope hood.

Example 3

Step-Wise Labeling Procedure and Sample Clean-Up

Hot and Cold Labeling

In the following, we describe the experimental procedure for the radiolabeling of 10 mg of FA with tritium. In addition, a batch of 110 mg of FA was treated with non-radioactive $NaBH_4$ following the same procedure with proportionally increased amounts of reagents. The resulting "cold-labeled" FA allowed for a detailed chemical characterization while minimizing safety restrictions.

Labeling Reaction

In preparation of the experiment, the Pt-catalyst was heated up to at least 115° C. with the air-flow set at 58.8 ml min$^{-1}$, the cooling-trap was filled with ice-water and the pH meter was calibrated using Science Workshop 2.2.5. The off-gas treatment was continuously run during the course of the experiment until the radiolabeled FA is removed from the closed reaction vessel.

A mass of 10 mg of FA was added to the reaction vessel by pipetting 1.95 ml of a previously prepared FA stock solution (5.13 g l$^{-1}$ FA) into the addition funnel, followed by carefully rinsing the funnel with exact volumes of autoclaved UV-water (1.5 ml).

In total, a mass of 10 mg (2.65E-04 moles) of $NaBH_4$ are needed to reach optimum reduction efficiency (see efficiency experiments), but only 7.6 mg of radioactive $NaBH_4$ were available. Hence, a mass of 2.4 mg of non-radioactive $NaBH_4$ was weighed out into a plastic centrifuge vial to provide the needed sodium borohydride excess concentration. A total volume of 0.5 ml of 0.1 N NaOH solution was added to the vials containing $NaBH_4$ in order to dissolve the reagent in a high-pH solution. From previous testing, it is known that this volume of 0.1 N NaOH will bring the final pH of the reaction solution to about 9.6 (data not reported). After both $NaBH_4$ solutions are transferred into the gas-tight addition funnel, the $NaBH_4$ vials were repeatedly rinsed with known amounts of autoclaved UV-water to bring the total volume of the $NaBH_4$ solution in the funnel to 4 ml. After short mixing, 5 µl of the $NaBH_4$ solution are taken out for later determination of the tritium counting efficiency of the liquid scintillation counter (see Example 5: Determination of specific activity of radiolabeled FA). The remaining solution was then transferred into the reaction vial, followed by additional UV-water rinses of the $NaBH_4$ vials and the addition funnel (2.554 ml), in order to bring the total volume of the reaction solution to 10 ml.

The pH probe and thermocouple were submersed into the reaction solution and the monitoring of solution conditions was started. First, the reaction was allowed to proceed under stirring at room temperature for 30 minutes. Then UV-water was added to the water-bath and heated to 60° C., and the reaction was allowed to proceed for four additional hours at elevated temperature.

First $NaBH_4$ Clean-Up Step: Na$^+$ Removal

After a total reaction time of 4.5 hours, a water-slurry of preconditioned cation exchange resin in the hydrogen form was added through the addition funnel into the reaction vessel. The resin provides reactive sites for the uptake of Na$^+$ originating from $NaBH_4$ in solution in exchange for H$^+$ in approximately ten-fold excess. Due to the proton release from the resin, a significant decrease of solution pH is observed.

Destabilization of Unstable Reaction Products

For the controlled destabilization of unstable reaction products and the removal of free tritium ions in solution, zero-grade air was sparged through the reaction solution until the water in the reaction vessel was completely dried out. For this purpose, a pipette tip attached to the inlet gas tubing was submersed into solution, while the temperature of the water bath was kept at around 45° C. Previous experimental testing based on the UV/VIS absorbance of FA solutions determined that air-sparging over at least 24 hours was sufficient for the complete reoxidation of unstable reduction products (data not reported). It was assumed that, after this step, the tritium remaining in the reaction vessel is associated with the FA in a stable, covalent bond.

Resin Separation from Solution

Autoclaved UV-water was added to redissolve FA and remove it from the reaction vessel. Then, the resin was separated from solution in a series of ten decanting steps followed by centrifugation (Baxter Biofuge 22 R, 30 min. at 10,000 rpm) and two-times filtration (0.7 µm Ahlstrom glass microfiber filter). The remaining FA solution was dried in a rotary evaporator flask.

Second $NaBH_4$ Clean-Up Step: Boric Acid Removal

In order to clean up the remaining boric acid ($B(OH)_3$) in solution, 5 ml of methanol (Optima Grade, Fisher Chemical: A454-4) were added to the dry sample to form the volatile trimethyl borate ($B(OCH_3)_3$), which was then removed by rotoevaporation (Büchi Rotovapor R). Methanol, however, can potentially methylate and permanently block relevant reactive groups of FA over time. Therefore, the rotoevaporation setup was optimized and tested beforehand to limit the contact time between FA and methanol to five minutes. The improved rotovap setup included the following additional features: cooling-water at 1-2° C. from a temperature-regulated water bath was circulated through the condenser; the condenser was wrapped with a wet cloth; the distillation tube was heated with a heating gun before and during rotoevaporation; the sample flask was rotated at high speed (setting: 9) in the hot water bath at 80° C.; and the collection flask was partially submersed into ice-water. After the removal of $B(OCH_3)_3$ and excess methanol, autoclaved UV-water was added to the sample flask immediately, and the radiolabeled FA was completely redissolved under shaking.

Sample Preservation

"Cold-labeled" FA was freeze-dried (Labconco Freeze Dryer 4.5) prior to storage. The radiolabeled FA product was stored frozen. Both samples were kept in the dark to prevent photocatalytic reactions. In addition, it is recommended to remove dissolved oxygen from FA solutions by sparging to minimize potential reoxidation reactions with dissolved oxygen.

Example 4

Labeling Efficiency Experiments and Modeling

As part of the optimization of the labeling procedure, the efficiency of the reduction reaction during labeling was determined experimentally as a function of sodium borohydride ($NaBH_4$) concentrations in solution. Due to the instability of the formed hydroquinones/phenols, there is a need to clearly define the term reduction efficiency. Maximum reduction efficiency is achieved when all FA reactive groups available for carbonyl reduction by $NaBH_4$ (ketones, as well as quinones) are completely reduced. The specific activity of the labeled product, however, is only based on the labeling of ketones due to their long-term stability.

In efficiency experiments, constant amounts of fulvic acid (FA) were reduced with various concentrations of $NaBH_4$, and the reaction solutions were analyzed for UV/VIS absorbance after complete reaction. UV/VIS spectral analysis was used since the reduction of quinones is known to result in a decrease in light absorbance and visual color of FA. Assuming that the number of transformed quinone groups is proportional to the total number of reduced FA carbonyl groups, the results of UV/VIS spectral analysis can be used to determine reduction efficiencies as function of $NaBH_4$ concentration and to optimize the labeling setup accordingly.

Furthermore, mathematical and chemical models were developed based on the fitting of model equations to the experimental absorbance data. These models were then applied to predict reduction efficiencies as a function of $NaBH_4$ concentrations in solution. As such, they provide a tool for the tailoring of this method to future applications; e.g., to produce radiolabeled fulvic acid (FA) of various specific activities or to label other types of organic matter. The latter requires that the organic material of interest has known concentrations of reactive groups suitable for the reduction with $NaBH_4$, such as aldehydes or ketones. Using these models, the transfer of this labeling technique to new applications is relatively simple and the chemical characteristics of the radiolabeled products are predictable.

Experimental

As quinone reduction products are unstable in aerobic environments over time, efficiency experiments were performed in an oxygen-free glove box environment and exposure of the samples to oxygen prior to UV/VIS scans is minimized. Further, oxygen-free UV-water was used in all reaction solutions. The water was prepared by boiling distilled UV-water for at least 45 minutes followed by cooling in ice-water for about 40 minutes, both under nitrogen purging of the solution. Prior to its use, the water was allowed to equilibrate with the oxygen-free atmosphere (5% hydrogen, balance nitrogen, General Air CGA 350) of the glove box for approximately 24 hours.

Aliquots of 10 mg of freeze-dried Suwannee River fulvic acid (FA) (International Humic Substances Society, Cat. No. 1 R101F-1) and various weights of non-radioactive sodium borohydride (CAS 16940-66-2, Fisher Chemical S678-25) from approximately 1.25 to 15 mg were weighed (METLER microscale). The plastic weighing boats were covered with aluminum foil to minimize weight losses due to electrostatic effects. All solids were moved into the oxygen-free glove box, where the reaction solutions were prepared in the following manner: The reactants and 9 ml of oxygen-free UV-water were transferred into acid-washed glass vials, and the pH value of each reaction solution was adjusted to 9.6±0.06 by adding small volumes of dilute sodium hydroxide and hydrochloric acid solutions. Then, the total volume of each sample was brought up to 10 ml and the sample vials were transferred into a water-bath, which had been preheated to 60° C. on a heating plate. Each sample solution was stirred at 60° C. during a total reaction time of four hours.

At the end of the reaction, the closed vials were removed from the glove box, rapidly cooled using tap water and weighed (AND ER-60A electronic balance). Volume losses due to evaporation were corrected, based on a weight-comparison, by adding small amounts of oxygen-free UV water. Within ten minutes or less after sample removal from the glove box, each sample solution was scanned on a Hach DR/4000 U Spectrophotometer over a wavelength range from 200 to 800 nm (rectangular, open-top, 10 mm far UV quartz cell: Hach Co. 48228-00, 1-Q-10). Oxygen-free UV-water adjusted to pH 9.6±0.03 provided the baseline for all UV/VIS scans. The solution absorbances at 465 nm were used to determine the reduction efficiencies at various $NaBH_4$ concentrations. This particular wavelength was chosen because it has shown significant absorbance differences between solutions of different $NaBH_4$ concentrations and its application for humic substances is well established in literature (MacCarthy, P. and J. A. Rice (1985). Spectroscopic methods (other than NMR) for determining functionality in humic substances. *Humic substances in soil, sediment and water*. G. R. Aiken, D. M. McKnight, R. L. Wershaw and P. MacCarthy. New York, John Wiley & Sons: 527-559). However, when absorbance data sets at different wavelengths (400 and 450 nm) were processed in the same manner, the predicted efficiency values were within 5 percent points of the predicted values for 465 nm absorbance data (data not reported).

After UV/VIS scanning, all solutions were exposed to the atmosphere and aerated with filtered building air through glass Pasteur pipettes for the reoxidation of unstable reduction products. The aeration process was stopped at repeated times for additional UV/VIS scanning after a weight correction for evaporation losses with UV-water. Based on these UV/VIS scans, the reoxidation of unstable products was complete after 24 hours (data not shown).

Example 5

Determination of Specific Activity of Radiolabeled FA

Tritium counting efficiency for sodium borohydride was determined in the following manner. During the labeling experiment, 5 µL of the 4 mL $NaBH_4$ solution in the addition funnel (100 mCi of tritiated $NaBH_4$ and approximately 2.4 mg of cold $NaBH_4$ in 0.0125 N NaOH) were removed from solution (10 µL Agilent tapered needle syringe, HP5181-1267) and diluted with 0.001 N NaOH in two steps, giving 5 µCi $ml^{-1}$ and 5 nCi $ml^{-1}$ tritium in solution. The low activity solution was used to count a series of $NaBH_4$ volumes in Ultima Gold XR liquid scintillation cocktail on a Perkin-Elmer TR 2500 liquid scintillation counter (LSC).

For the determination of the specific activity of the radiolabeled FA product, fractions of a 1:50 dilution of the original radiolabeled FA stock solution were analyzed for Total Organic Carbon (TOC) (Shimadzu TOC 5000, high-sensitivity catalyst), and for tritium activity (Perkin-Elmer TR 2500 LSC).

The calculated tritium counting efficiency under the specified conditions is 0.4769 with an estimated total error of ±4.16%. The tritium activity of the radiolabeled FA stock solution is computed as 0.62 mCi $ml^{-1}$ (22.94 MBq $ml^{-1}$) ±3.46%. Based on a fulvic acid TOC content of 53.49%

(Averett et al., 1994), this gives a specific activity of 1.89 mCi mg$^{-1}$ FA (69.93 MBq mg$^{-1}$ FA)±4.91%. The resulting detection limit for FA concentrations in solution is 0.31 µg l$^{-1}$ FA (4.4E-10 mol l$^{-1}$ FA, 0.16 µg l$^{-1}$ TOC).

For the analysis of the exact FA activity, FA chemiluminescence effects during counting were neglected, since only small volumes of low FA concentrations were added to LSC cocktail, and as the number of total counts was very high. However, potentially increased background values have to be expected for samples of high fulvic acid concentrations. As these luminescence effects may be dependent on solution conditions, such as FA concentration, pH, etc., an individual characterization for specific applications is recommended.

Example 6

Comparison of FTIR Spectra

A comparison of FTIR spectra of the original, untreated FA stock with cold-labeled FA allowed us to investigate potential changes in the FA functional group composition due to labeling. In particular, we needed to ensure that FA carboxyl groups had not been methylated to methyl esters during the rotoevaporation step with methanol (peaks at 1740, 1439, and 1170 cm$^{-1}$) Furthermore, the cold-labeled FA spectra were examined for potential methanol (1033 cm$^{-1}$) and boric acid (3200, 1194, and 548 cm$^{-1}$) impurities.

Samples of original, untreated FA and cold-labeled, freeze-dried FA were dried over desiccant for approximately 48 hours. From each FA sample, approximately 2 mg were mixed with 100 mg potassium bromide (KBr, Sigma-Aldrich, 99+%, FT-IR grade, 221864-25 g), and pressed to pellets (Carver hydraulic unit, model #3925). The FTIR spectra of the FA samples and a KBr blank are collected over the mid-IR region (4000-400 cm$^{-1}$) with 200 scans at 2 cm$^{-1}$ resolution (Nexus 670 FT-IR ESP). The instrument performs an automatic blank subtraction.

The transmittance spectrum of untreated FA agrees well with literature data (MacCarthy and Rice, 1985), while the spectrum of the cold-labeled FA shows a few additional peaks that can be explained by the creation of aliphatic hydroxyl groups from the reduction of aliphatic ketones. The more pronounced peak in the 3400 cm$^{-1}$ region is caused by the OH groups of created aliphatic alcohols. The sharp peaks from 1100 to 1050 cm$^{-1}$ are the C—O stretches of these created alcohols. There is no evidence of the formation of methyl esters or of boric acid impurities. A slight methanol contamination, however, may be present.

Example 7

NMR Spectral Analysis

Proton NMR analysis of cold-labeled FA was used to confirm the reduction of aliphatic and aromatic ketones to secondary alcohols by sodium borohydride. In addition, it allowed for the determination of potential methanol contamination in the reduced FA sample.

Approximately 17 mg of untreated FA and cold-labeled FA were dissolved in 0.9 ml of deuterium oxide (HDO, Cambridge Isotope Products, 99.9%, DLM-4) to give a concentration of 18.89 mg ml$^{-1}$. Proton NMR spectra were generated on a Chemomagnetics CMX Infinity 400 Solids/Liquids NMR Spectrometer operating at 400 MHz, with a pulse delay of 1 sec.

Figure 5:
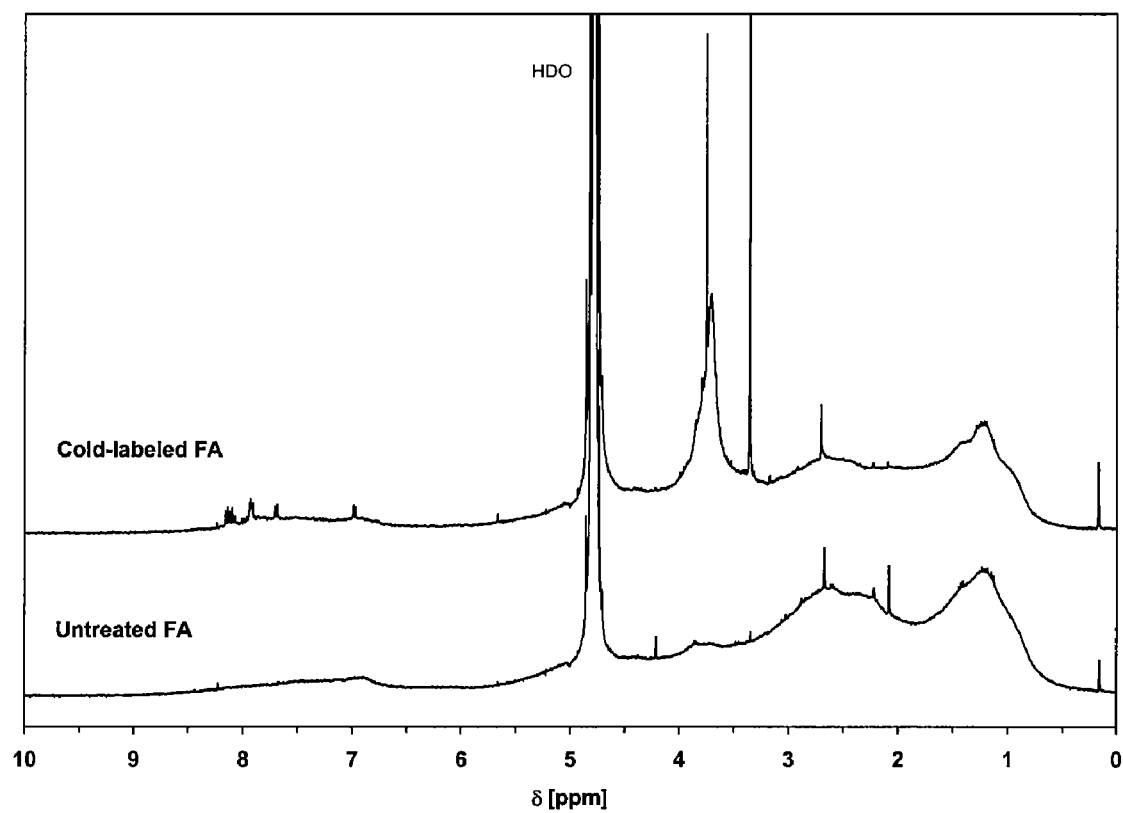
FIG. 5 depicts proton NMR spectra of cold-labeled and untreated FA.

The $^1$H-NMR spectrum of cold-labeled FA (FIG. 5) shows a substantial decrease in the broad 2.7-ppm peak and a substantial increase in the 1.25-ppm peak in comparison to untreated FA, as has been described for the reduction of FA with NaBH$_4$ previously (Leenheer et al., 1987). Further, the valley at 1.7 ppm in the reduced FA sample is less pronounced than for the original FA. The latter indicates that methylene hydrogen, adjacent to aromatic ketones, has been converted to methylene, adjacent to aromatic carbinols. All of these observations confirm the reaction mechanism described in detail earlier.

The spectrum of cold-labeled FA also shows a sharp peak at 3.34 ppm, which was identified as methanol contamination (NMR solvent data chart, Cambridge Isotope Laboratories, Inc.), probably due to the FA contact with methanol during rotoevaporation. Based on a rough estimation, the methanol impurity contributes about 8% of the total number of protons in the cold-labeled FA sample. We assume for now that a similar level of methanol contamination can be expected in tritium-labeled FA.

Example 8

Characterization by Size Exclusion Chromatography

FA characterization by size exclusion chromatography (SEC) was performed to investigate two aspects of the label: (1) the distribution of the tritium label over the molecular size range of FA; and (2) label stability during short-term experimental conditions and long-term storage.

Samples were injected into a Universal Fractionator (Model F-1000 FFFractionation, Inc.) with a home-built injection loop (approximately 200 µl) connected to a TSK-50S size exclusion chromatography column (8×300 mm, 30 µm particles) (Her, N.; Amy, G.; Foss, D.; Cho, J.; Yoon, Y.; Kosenka, P. Optimization of method for detecting and characterizing NOM by HPLC—size exclusion chromatography with UV and on-line DOC detection. *Environ. Sci. Technol.* 2002, 36, 1069-1076). A Na$_2$HPO$_4$ buffer was used as carrier solution (0.004 M Na$_2$HPO$_4$ in 0.088 M NaCl, I$_{TOT}$=0.1 M, pH approximately 8.3) at 0.7 ml min$^{-1}$ (Acuflow Series II pump). A 254 nm UV measuring cell (ISCO Type-II Optical Unit) coupled with a UV/VIS detector (ISCO Model 229) provided online recording of the UV-absorbance with Flow 2003 software. Eluent fractions were also collected for highly concentrated FA samples and tritiated FA samples for TOC analysis (Shimadzu TOC 5000, regular sensitivity catalyst) or tritium counting (Perkin-Elmer TR2500 LSC). Prior to sample characterization, the molecular size separation of the column was calibrated based on the injection of a series of polyethylene glycol/polyethylene oxide molecular size standards from 400 to 12,600 Da.

Initially, three sample solutions were prepared in the buffer matrix for the comparison of their SEC profiles: tritiated FA at a concentration of approximately 10 mg l$^{-1}$ TOC and two regular FA samples of approximately 10 and 200 mg l$^{-1}$ TOC. After SEC sample characterization over four days, the solutions were split up into three volume fractions each, and individually adjusted to specific pH values of 4, 7 or 10. Then, solutions were allowed to "age" on a shaker table at room temperature for approximately 10.5 days (253 hours).

Finally, solution pH values after shaking were recorded and re-adjusted to the original values prior to adjustment, followed by a second sample characterization by SEC.

In addition to short-term stability, the long-term behavior of the label was also tested based on SEC characterization of a tritiated FA dilution (12.4 µCi (0.46 MBq) ml$^{-1}$; 6.56 mg l$^{-1}$ FA, pH=6.65) stored at 4° C. for approximately 21 months.

Figure 7:
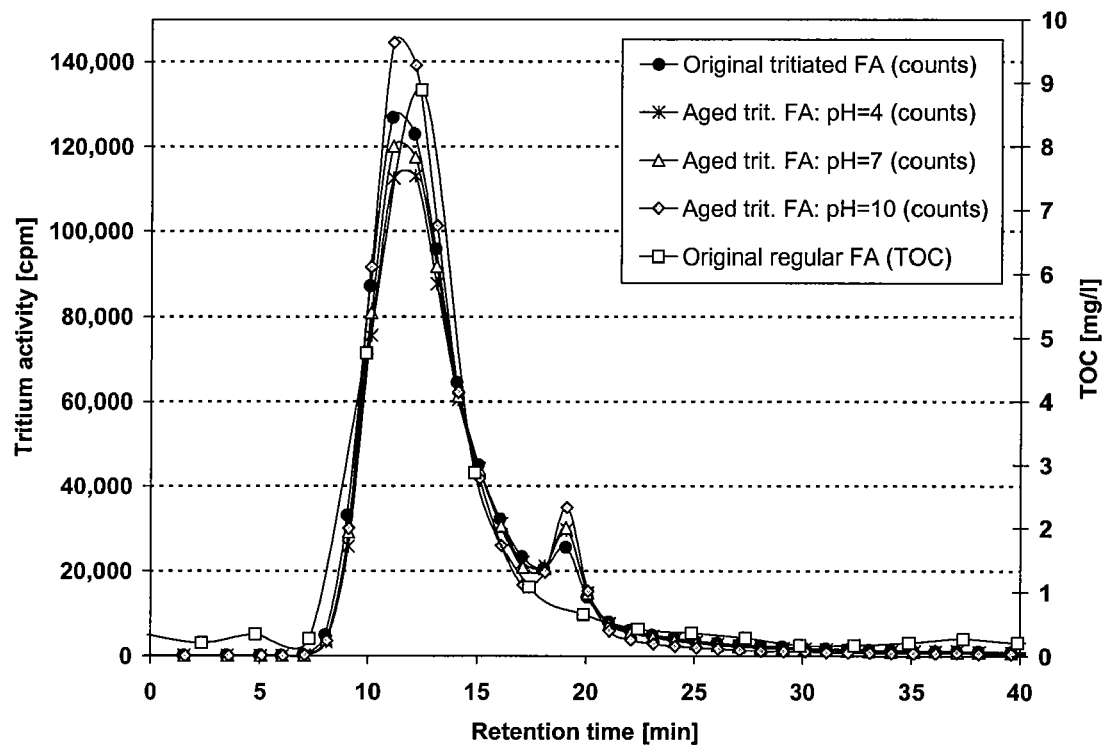
FIG. 7 depicts size exclusion chromatograms of various FA samples based on TOC analysis or tritium counting.
Figure 8:
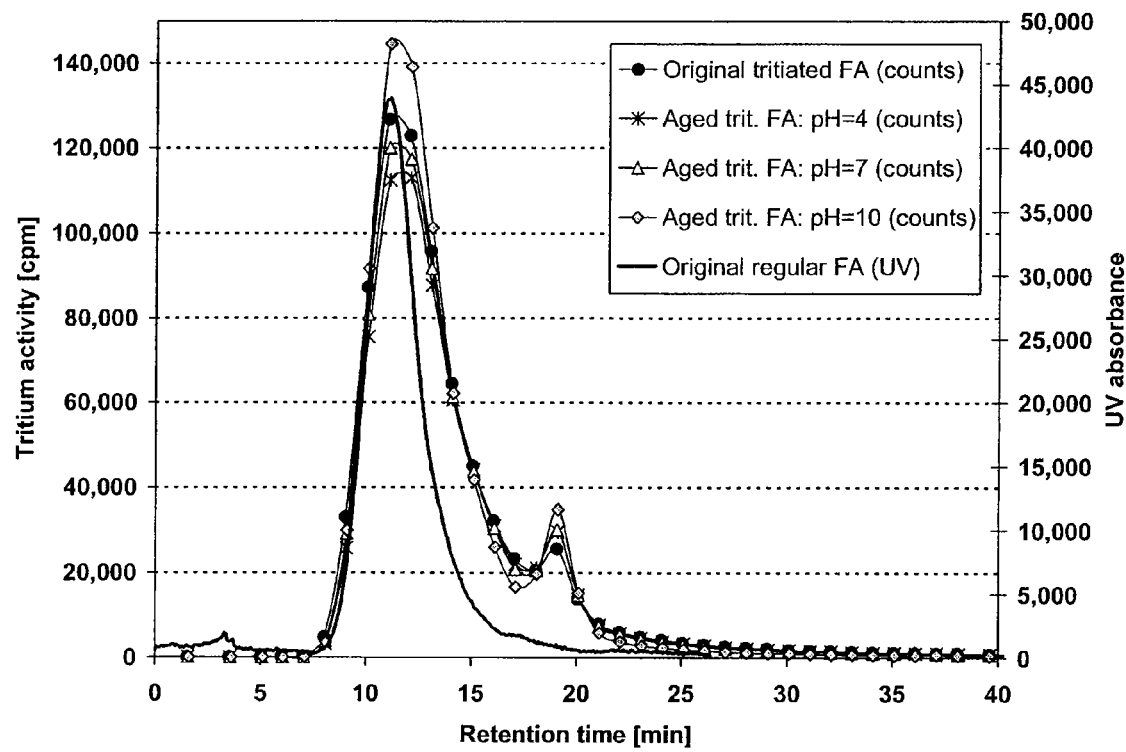
FIG. 8 depicts size exclusion chromatograms of various FA samples analyzed by online UV-absorbance or tritium counting.

The SEC results show that the size distribution of radiolabeled FA determined by tritium counting follows FA chromatograms based on TOC and UV-absorbance data (FIG. 7 and FIG. 8). Note, however, that the UV-signal of regular FA does not follow the FA size distribution in the low molecular size region. This is probably due to the fact that small MW compounds of FA have low UV-absorbance, which excludes UV-absorbance measurements as an appropriate characterization tool for FA mass contributions in various size fractions in this molecular size range. Generally, however, the results indicate an even distribution of the tritium label over the molecular size range as well as the conservation of the original FA size distribution during the labeling process. However, an additional small peak at 19.1 minutes retention time was detected for tritiated FA indicating a tritium-based impurity of approximately 3% (m/m) in the MW size range of 100 Da. This impurity concentration can be assumed to be negligible for most tracer applications of radiolabeled fulvic acid.

Figure 9:
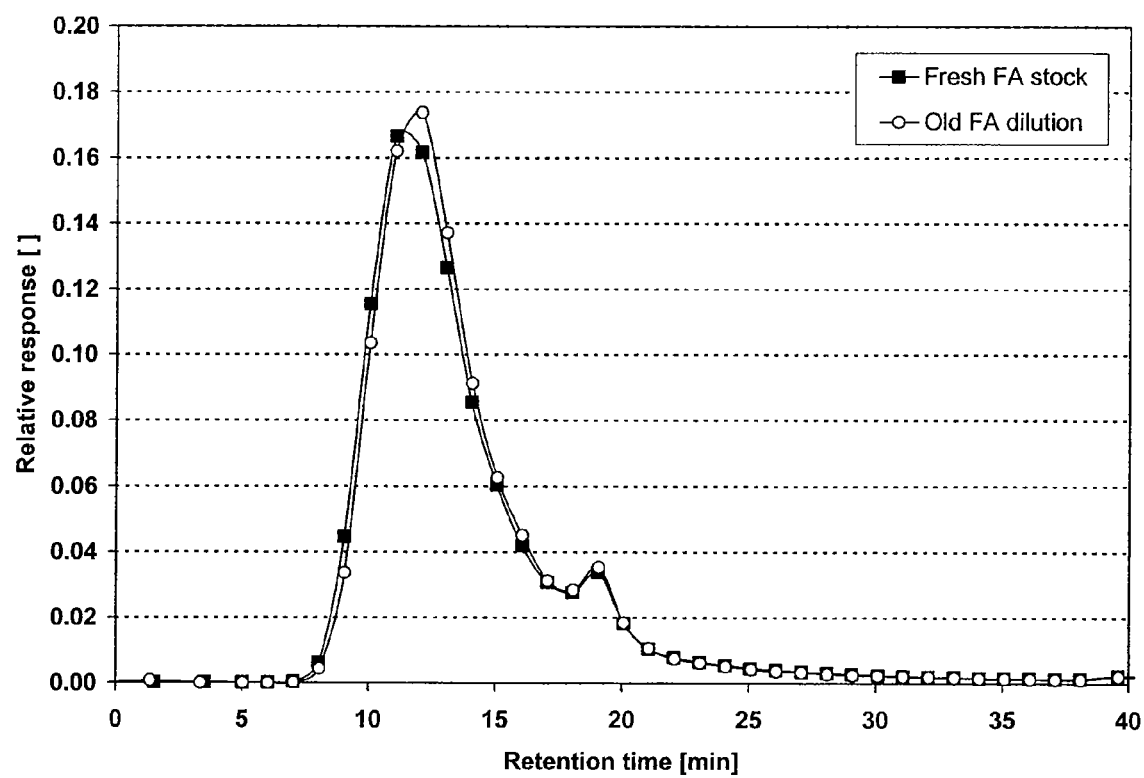
FIG. 9 depicts the normalized size exclusion chromatograms of a fresh dilution of tritiated FA stock and an old, tritiated FA dilution sample stored in the refrigerator at its natural pH (6.65) for over 21 months.

During sample aging, solution pH was stable (±0.3) except for the pH 10 samples, which showed a pH decrease to approximately 9.4. SEC chromatograms of aged tritiated FA samples showed very good agreement with the size distribution of original FA samples. A significant dissociation or exchange of the tritium label has not been detected, besides a potential small increase in the tritium-based impurity (maximum contribution of 5%). Furthermore, the size distribution of the 21-month-old tritiated FA dilution follows the chromatogram of the tritiated FA stock very well, indicating long-term stability of the label during storage (FIG. 9).

Example 9

Comparison of FA Sorption Behavior

FA sorption behavior was investigated to determine whether the FA sorption was altered due to the labeling procedure. Indirectly, the experimental setup also allows testing of the chemical stability of the label over a wide pH range.

Generally, following the procedure by Lenhart and Honeyman (Lenhart, J. J. and B. D. Honeyman (1999). "Uranium (VI) sorption to hematite in the presence of humic acid." *Geochimica Et Cosmochimica Acta* 63(19-20): 2891-2901), a total concentration of 10 mg l$^{-1}$ FA was sorbed to 1 g l$^{-1}$ hematite in a series of sample vials, each representing a different solution pH, for 51 hours. FA samples contain either unaltered FA or cold-labeled FA combined with small volumes of tritium-labeled FA (10 µl of 12.4 µCi ml$^{-1}$) in 25 ml total volume. The total ionic strength (I) for samples of pH<6 was 0.01 N NaClO$_4$/NaHCO$_3$; for solutions at higher pH it was slightly higher (pH=7, I=0.011 N; pH=7.5 N, I=0.012; pH=8, I=0.017 N; pH=9, I=0.029 N). This is different from the published procedure, where all sample solutions were kept at the same constant ionic strength.

After equilibration, pH measurement and sample centrifugation (Baxter Biofuge 22R, at 10,000 rpm for 159 min., T=25° C.), volume fractions of the supernatant solutions were analyzed for FA in terms of TOC (Shimadzu TOC 5000, high sensitivity catalyst) or tritium activity (Perkin-Elmer LSC TR2500). The fraction of FA sorbed to the mineral phase was calculated based on FA concentrations in standard vials containing no solid phase (100% FA in solution).

Figure 6:
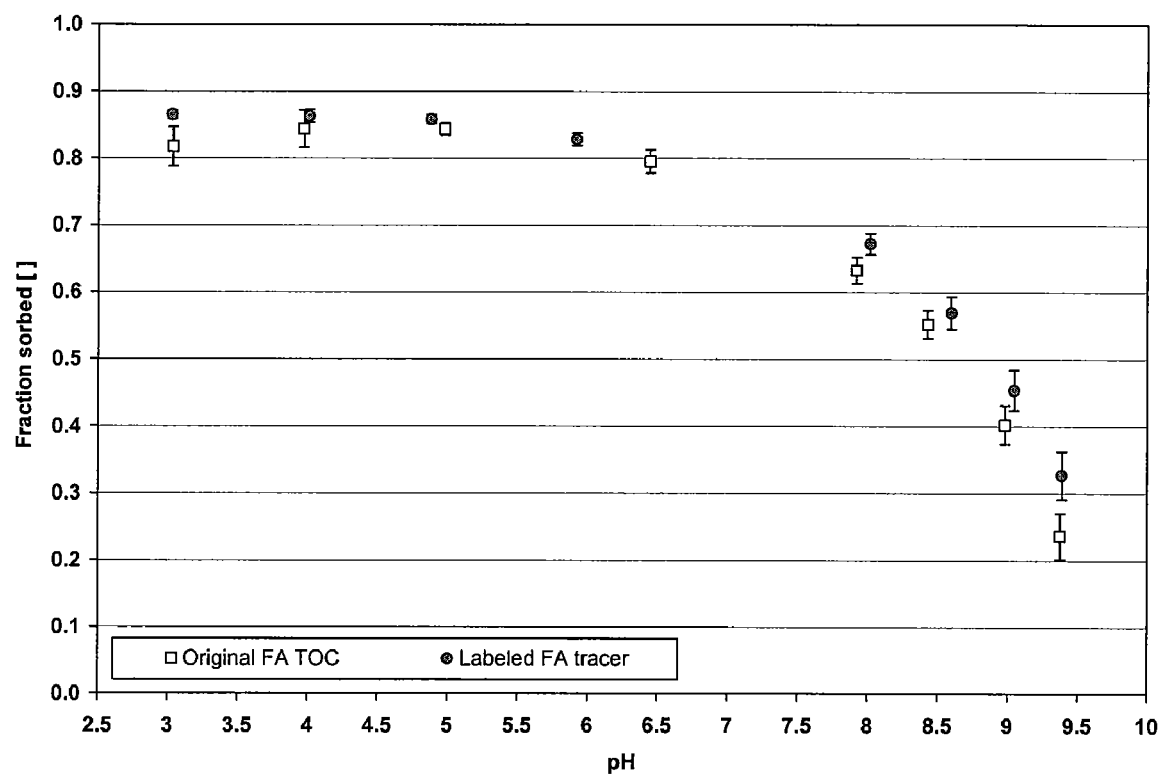
FIG. 6 depicts the sorption of 10 mg $l^{-1}$ FA to 1 g $l^{-1}$ hematite at an ionic strength of $I=0.01N$ $NaClO_4/NaHCO_3$. Experimental results are based on TOC measurements or on counting of tritium-labeled FA tracer. Error bars represent standard deviations of analytical measurements.

The results for FA sorption to hematite based on the tritium counting data of the radiolabeled FA tracer show very good agreement with sorption data determined by TOC measurements (FIG. 6). Potential small methanol impurities in the tritium-labeled FA tracer do not affect FA sorption behavior. Based on this result, we can further conclude that tritium-labeled FA is chemically stable in solution and in the presence of an iron mineral phase over a wide pH range.

Example 10

Labeling Efficiency Experiments and Modeling

Figure 3:
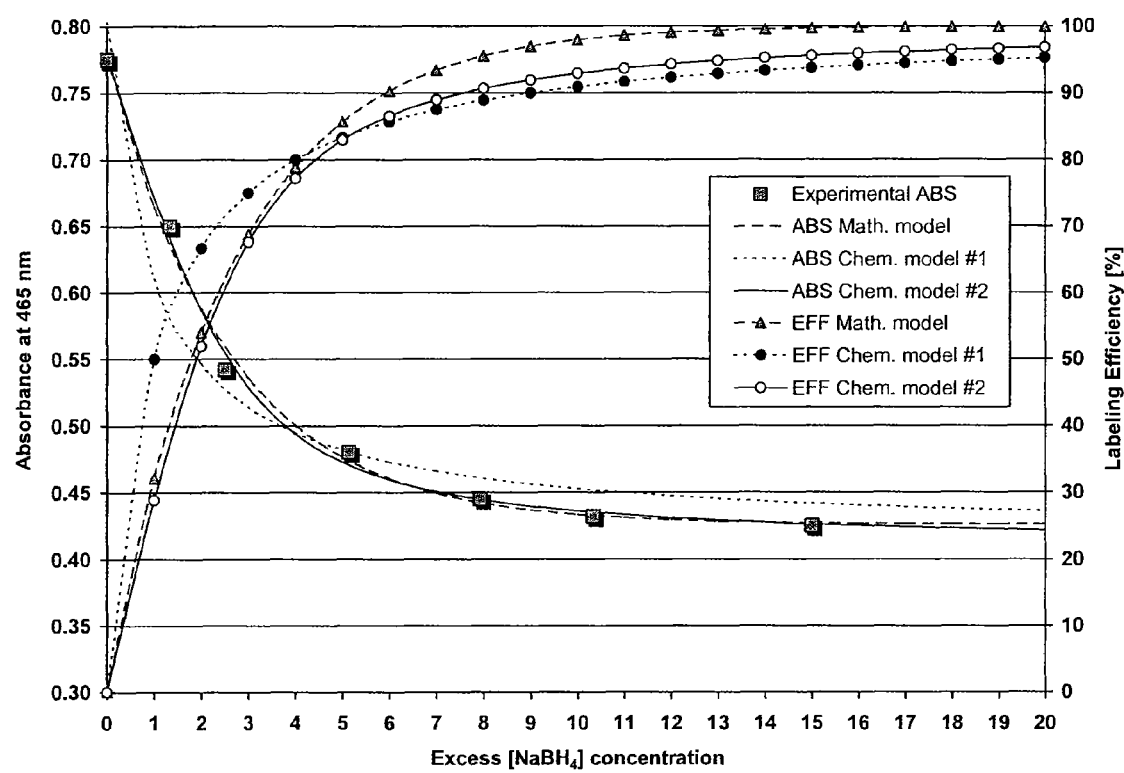
FIG. 3 depicts the experimental data and model fits for (1) fulvic acid (FA) absorbance at 465 nm (ABS) as a function of excess $NaBH_4$ concentration in solution and (2) model predictions for reduction efficiency (EFF) as a function of excess $NaBH_4$ concentration in solution.
Figure 4:
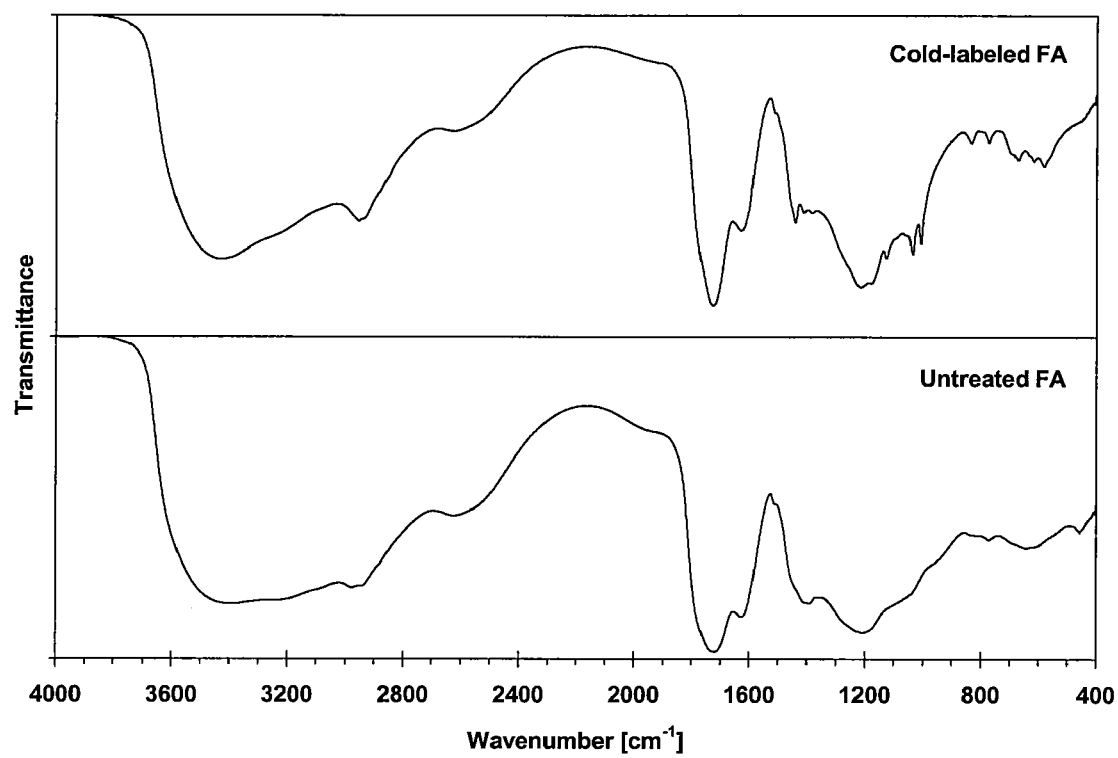
FIG. 4 depicts FTIR spectra of original and cold-labeled FA.

The UV/VIS absorbance spectra for FA blank solutions (no NaBH$_4$ added) agree well with literature data (MacCarthy and Rice, 1985). The absorbance data at 465 nm show an exponential-type decrease in absorbance with increasing NaBH$_4$ excess concentrations in solution. Due to the assumption of a linear relationship between solution absorbance and reduction efficiency, this leads to the prediction of an exponential-type increase in reduction efficiencies with increasing NaBH$_4$ excess concentrations (FIG. 3).

All three model fits follow the general trend of the absorbance data reasonably well, which implies that, despite their simplicity, the proposed chemical models describe the chemical system behavior sufficiently well. For a more detailed model analysis, the Root Mean Square (RMS) is used as a goodness-of-fit estimate to compare model fits based on the overall variance of residuals:

$$RMS = \sqrt{\frac{\sum_{i=1}^{N} (ABS_i - ABS_{i,\exp})}{(N - P)}} \quad \text{(Equ. 32)}$$

with $ABS_i$ ... Model fit of absorbance value
$ABS_{i,exp}$ ... Experimental absorbance value
N ... Number of data points
P ... Number of model fitting parameters The smaller the RMS value is for a particular model, the more closely this model simulates the absorbance data points. Based on calculations, chemical model #2 provides the best fit (RMS=1.076E−02) of the absorbance data, the mathematical model the second best (RMS=1.175E−02), and chemical model #1 the third best (RMS=4.006E−02). In addition to a higher RMS value, chemical model #1 also shows structure in the residuals. The improved fit of chemical model #2 over chemical model #1 indicates that the actual concentration of FA-reactive groups involved in the reduction reaction may be larger than the FA-ketone group concentration ($\alpha_o$>1). However, an improved fit of chemical model #2 is also expected due to the fact that this model included one additional fitting parameter in comparison to the other two models. Therefore, additional data points and replicates are needed to support this conjecture, which goes beyond the scope of this study.

For the prediction of reduction efficiencies, the fitted model absorbance curves are mathematically converted into efficiency curves. This conversion is based on the modeled fitting parameters rather than experimental data to minimize the effects of experimental error, and to ensure that the predicted efficiencies are exclusively determined from model calculations. Further, it was specified that predicted efficiency values smaller than zero and larger than 100 percent would not be accepted.

For the mathematical model, the fitting parameters for the absorbance curve, $a_1$, $b_1$, and $c_1$, were linked to the efficiency function using the assumption of a linear relationship between efficiency and absorbance:

$$E = -k \times ABS + d = -\frac{ABS}{a} + d \text{ with } a = \frac{1}{k} \quad \text{(Equ. 33)}$$

The combination of $ABS = a_1 + b_1 \exp(-c_1 x)$ with this linear relationship, gives $$E = -\frac{a_1 + b_1 \times \exp(-c_1 x)}{a} + d \quad \text{(Equ. 34)}$$

This equation is solved for the variables a and d by using two boundary conditions: 1) for $x \to 0$, $E \to 0$, and 2) for $x \to \infty$, $E \to 1$, which results in $a = b_1$ and $$d = \frac{a_1 + b_1}{b_1}.$$

The substitution of these expressions for the variables a and d in equation 34, leads to the efficiency expression for the mathematical model:

$$E(x) = 1 - \exp(-c_1 x) \quad \text{(Equ. 35)}$$

For both chemical models, the linear relationship between light absorbance and efficiency has already been used in their mathematical derivations. Therefore, expressions for the variables a and d can be directly derived from the original definition of the absorbance fitting parameters, $\beta_0$, $\beta_1$, and $\gamma_1$:

$$\beta_0 = ad, \beta_1 = \frac{ab}{2}, \text{ and } \gamma_1 = \frac{4}{b}.$$

The resulting expressions for $$a = \frac{\beta_1 \gamma_1}{2} \text{ and } d = \frac{2\beta_0}{\beta_1 \gamma_1}$$

are combined with equation 33 to give the efficiency functions for chemical model #1 and #2 (FIG. 3, Table 1):

$$E(x) = \frac{2\{\beta_0 - ABS(x)\}}{\beta_1 \gamma_1} \quad \text{(Equ. 36)}$$

It is concluded that at least a ten-fold molar $NaBH_4$ excess concentration, equivalent to approximately equal masses of FA and $NaBH_4$, is required to ensure maximum reduction efficiency of FA-ketone groups.

TABLE 1

Labeling efficiency experiments
Experimental results

| Sample ID | Total FA [mg] | Total ketones [mol] | Total $NaBH_4$ [mg] | Total $NaBH_4$ [mol] | Excess $NaBH_4$ (=x) [mol $NaBH_4$/mol ket.] | Absorbance at 465 nm [ ] |
|---|---|---|---|---|---|---|
| Blank | 10.154 | 2.640E-05 | 0 | 0 | 0.000 | 0.775 |
| 1 | 10.039 | 2.610E-05 | 1.316 | 3.478E-05 | 1.333 | 0.650 |
| 2 | 10.136 | 2.635E-05 | 2.497 | 6.600E-05 | 2.504 | 0.542 |
| 3 | 10.196 | 2.651E-05 | 5.151 | 1.362E-04 | 5.136 | 0.480 |
| 4 | 10.153 | 2.640E-05 | 7.914 | 2.092E-04 | 7.924 | 0.445 |
| 5 | 10.143 | 2.637E-05 | 10.302 | 2.723E-04 | 10.326 | 0.432 |
| 6 | 10.197 | 2.651E-05 | 15.041 | 3.976E-04 | 14.996 | 0.425 |

Modeling summary and results

| Model | Absorbance equation | Fitting parameters | Efficiency equation | RMS*) |
|---|---|---|---|---|
| Math.. | $ABS = a_1 + b_1 \exp(-c_1 x)$ | $a_1 = 0.42618$<br>$b_1 = 0.351736$<br>$c_1 = 0.388445$ | $E(x) = 1 - \exp(-c_1 x)$ | 1.175E-02 |
| Chem. #1 | $ABS = \beta_0 - \beta_1\{(x+1) - \sqrt{(x+1)^2 - \gamma_1 x}\}$ | $\beta_0 = 0.803126$<br>$\beta_1 = 1171.41$<br>$\gamma_1 = 0.0006579$ | $E(x) = \frac{2\{\beta_0 - ABS(x)\}}{\beta_1 \gamma_1}$ | 4.006E-02 |
| Chem. #2 | $ABS = \beta_0 - \beta_1\{(x+1) - \sqrt{(x+1)^2 - \gamma_1 x}\}$ | $\beta_0 = 0.777459$<br>$\beta_1 = 0.223426$<br>$\gamma_1 = 3.28856$<br>$\alpha = 0.309356$ | $E(x) = \frac{2\{\beta_0 - ABS(x)\}}{\beta_1 \gamma_1}$ | 1.076E-02 |

*) RMS = Root Mean Square (see text for details)

Example 11

A Method for the Extraction of Humic Substances from Soil Developed by the International Humic Substances Society (IHSS) (http://www.ihss.gatech.edu)

Materials
1. Hydrochloric acid (HCl), 1 M, 6 M
2. Sodium hydroxide, 1 M, 0.1 M
3. Potassium hydroxide (KOH), 0.1 M
4. Potassium chloride (KCl)
5. Hydrofluoric acid (HF) concentrated, 0.3 M
6. XAD-8 resin (Rohm & Haas Co., Philadelphia, Pa.)
7. Visking dialysis tubing (Visking Co., Chicago, Ill.) [MWCO (molecular weight cut-off)] 10,000 dalton Method Remove roots and sieve the dried soil sample to pass a 2.0-mm sieve. Equilibrate the sample to a pH value between 1 to 2 with 1 M HCl at room temperature. Adjust the solution volume with 0.1 M HCl to provide a final concentration that has a ratio of 10 mL liquid/1 g dry sample. Shake the suspension for 1 h and then separate the supernatant from the residue by decantation after allowing the solution to settle or by low speed centrifugation. Save the supernatant (FA Extract 1) for the separation of fulvic acid using XAD-8.

Neutralize the soil residue with 1 M NaOH to pH=7.0 then add 0.1 M NaOH under an atmosphere of $N_2$ to give a final extractant to soil ratio of 10:1. Extract the suspension under $N_2$ with intermittent shaking for a minimum of 4 h. Allow the alkaline suspension to settle overnight and collect the supernatant by means of decantation or centrifugation. Acidify the supernatant with 6 M HCl with constant stirring to pH=1.0 and then allow the suspension to stand for 12 to 16 h. Centrifuge to separate the humic acid (precipitate) and fulvic acid (supernatant—FA Extract 2) fractions.

Redissolve the humic acid fraction by adding a minimum volume of 0.1 M KOH under $N_2$. Add solid KCl to attain a concentration of 0.3 M [$K^+$] and then centrifuge at high speed to remove the suspended solids. Reprecipitate the humic acid by adding 6 M HCl with constant stirring to pH=1.0 and allow the suspension to stand again for 12 to 16 h. Centrifuge and discard the supernatant. Suspend the humic acid precipitate in 0.1 M HCl/0.3 M HF solution in a plastic container and shake overnight at room temperature. Centrifuge and repeat the HCl/HF treatment, if necessary, until the ash content is below 1%. Transfer the precipitate to a Visking dialysis tube by slurrying with water and dialyze against distilled water until the dialysis water gives a negative Cl− test with silver nitrate $AgNO_3$. Freeze dry the humic acid.

Pass the supernatant designated "FA Extract 1" through a column of XAD-8 (0.15 mL of resin per gram of initial sample dry weight at a flow rate of 15 bed volumes per h). Discard the effluent, rinse the XAD-8 column containing sorbed fulvic acid with 0.65 column volumes of distilled $H_2O$. Back elute the XAD-8 column with 1 column volume of 0.1 M NaOH, followed by 2 to 3 column volumes of distilled $H_2O$. Immediately acidify the solution with 6 M HCl to pH=1.0. Add concentrated HF to a final concentration of 0.3 M HF. The solution volume should be sufficient to maintain the fulvic acid in solution.

Pass the supernatant designated "FA Extract 2" through a column of XAD-8 (1.0 mL of resin per gram of initial sample dry weight). Repeat the back elution and acidification as for "FA Extract 1" above. Combine the final eluates from each of the fulvic acid extracts and pass this solution through XAD-8 resin in a glass column (column volume should be one-fifth of sample volume). Rinse with 0.65 column volumes of distilled $H_2O$. Back elute with 1 column volume of 0.1 M NaOH followed by two column volumes of distilled $H_2O$. Pass the eluate through $H^+$-saturated cation exchange resin [Bio-Rad AG-MP-5 (Bio-Rad, Richmond, Calif.) using three times the mole of $Na^+$ ions in solution]. Freeze dry the eluate to recover the $H^+$-saturated fulvic acid.

It should be noted that there are alternative ways of implementing the disclosures contained herein. Accordingly, the present embodiments are to be considered as illustrative and not restrictive, and the claims are not to be limited to the details given herein, but may be modified within the scope and equivalents thereof.

What is claimed is:

1. A method of labeling natural organic matter (NOM) with a hydrogen label comprising:
   removing insoluble NOM from solubilized NOM;
   contacting said solubilized NOM with a tritiated or deuterated reducing agent to label said solubilized NOM with tritium or deuterium;
   aerating the labeled mixture to reoxidize unstable tritiated products; and
   removing any destabilized label by complete solution evaporation.

2. The method of claim 1, wherein NOM is humic acid (HA) or fulvic acid (FA).

3. The method of claim 1, wherein the tritiated or deuterated reducing agent is borohydride.

4. The method of claim 1, wherein the label is distributed substantially equally by molecular size.

5. The method according to claim 1, further comprising aerating the mixture to reoxidize unstable labeled NOM and removing of the destabilized label by complete solution evaporation.

6. A composition comprising tritiated NOM made according to the method of claim 1.

7. A composition comprising tritiated HA or tritiated FA made according to the method of claim 1.

8. A method for determining the concentration of natural organic matter (NOM) comprising:
   a) labeling said NOM according to the method of claim 1; and
   b) measuring the radioactivity of said labeled NOM and determining the concentration of said NOM.

9. The method of claim 8, wherein said determining further comprises comparing said measured radioactivity against the measured radioactivity of a tritiated NOM standard.

10. The method according to claim 8 further comprising c) aerating the mixture formed in step a) to reoxidize unstable tritiated products and removing of the destabilized label by complete solution evaporation.

11. The method according to claim 8, wherein said NOM comprises solubilized humic acid or solubilized fulvic acid.

12. The method according to claim 8, wherein said NOM comprises a ketone functionality and/or an aldehyde functionality.

* * * * *